US007300752B2

(12) United States Patent  
Ferrie et al.

(10) Patent No.: US 7,300,752 B2
(45) Date of Patent: Nov. 27, 2007

(54) COMPOSITIONS AND METHODS FOR DETERMINING CANINE GENDER

(75) Inventors: Bonita J. M. Ferrie, Vacaville, CA (US); Eric V. Johnston, Davis, CA (US); Sue DeNise, Davis, CA (US)

(73) Assignee: MMI Genomics, Inc., Davis, CA (US)

( * ) Notice: Subject to any disclaimer, the term of this patent is extended or adjusted under 35 U.S.C. 154(b) by 0 days.

(21) Appl. No.: 10/754,437

(22) Filed: Jan. 9, 2004

(65) Prior Publication Data

US 2004/0146915 A1    Jul. 29, 2004

Related U.S. Application Data

(60) Provisional application No. 60/439,188, filed on Jan. 10, 2003.

(51) Int. Cl.
  *C07H 21/04*  (2006.01)
  *C12Q 1/68*  (2006.01)
(52) U.S. Cl. .................. 435/6; 435/91.1; 435/91.2; 536/23.1; 536/24.3
(58) Field of Classification Search .............. 435/6, 435/91.1, 91.2; 536/23.1, 24.3
  See application file for complete search history.

(56) References Cited

U.S. PATENT DOCUMENTS 5,474,796 A    12/1995    Brennan

FOREIGN PATENT DOCUMENTS

WO    WO 03/004630 A2    1/2003

OTHER PUBLICATIONS

Genbank Accession No. AB80686, *Canis familiaris* amelx gene for amelogenin, Sep. 2002.*
Tachi et al. (J. of Reproduction and Development, vol. 48, No. 6, 2002).*
Asano et al. (Am. Sc. J., vol. 70, No. 10, pp. J351-J362, Oct. 1999)(see English abstract and Figures in English).*
Yuasa et al. (J. Comp. Path. vol. 199, pp. 15-25, 1998).*

* cited by examiner

*Primary Examiner*—Jeanine A. Goldberg
(74) *Attorney, Agent, or Firm*—DLA Piper US LLP

(57) ABSTRACT

The present invention provides methods to determine gender of a canine subject, that include contacting a nucleic acid sample from the canine subject with at least one probe or primer specific for canine amelogenin, and using the binding of the at least one probe or primer to detect a difference between the canine amelogenin gene on the Y chromosome and the canine amelogenin gene on the X chromosome, thereby determining gender of the canine subject. In certain aspects, gender of the canine subject is determined by contacting the nucleic acid sample with a primer pair that generate different sized amplification products depending on whether an X chromosome or a Y chromosome copy of the canine amelogenin gene is amplified. In certain aspects and embodiments disclosed herein, in addition to detecting binding of at least one probe or primer to a canine amelogenin gene, methods of the present invention include detecting binding of at least one probe or primer to a canine microsatellite locus, thus providing a genotyping and gender determination assay.

11 Claims, 6 Drawing Sheets

```
X 1-60      ATGGGGACCTGGATTTTGTTTGCCTGCCTCCTGGGAGCAGCCTTGGGTATGCCGGTGAGT
Y 1-60      ATGGGGACCTGGATTTTGTTTGCCTGCCTCCTGGGAGCAGCCTTCAGTATGCCTGTGAGT

X 61-117    AAAATACCCCTGCATAATATTCAATTTCACAAGCTTGGAAATAAAAGTCTGCC-CG-AC-
Y 61-114    AAAAT-----TTCG-AATTTGCAATTTCACAAGCTTGGAAATAAAATCTGCCTCAGATT

X 118-171   ---AGTT-GG-T-AAAGTTTAGGGTTTAAGACAGTACAAGATCAGATGTCCTCAAATGTG
Y 115-174   TTTATTTAGGGTTAAATTTAAGGGTTTAAGACAGTACAAGATCTGATGTTCACAAATGTG

X 172-223   TCTGTGTTTAAGAAACAGTTGGAAGAGCTTG-TTATAA-A----AAAA-AATAT-ATTCG
Y 175-234   ACTGTGTTTAAGAAACATTTTTAAAATCTTGATCAGAAGATTTTAAAACAAAAACATTCT

X 224-282   CAGTTGCCTCCACCCA-AGACTGATTCAGTAGAGCTGGAGTGGGGGATGCGGAGGACT
Y 235-294   CAGTTGCCTTCACCCATATTCTGATTCAGTATAGCCAGAGTGGGGGGTGCTGAGAACT

X 283-338   CTGGATTTTAACAAGCA----CCTCAGGAGATTCTGTGGAGACAATTAACTTGTAAATAT
Y 295-347   CTGAATTTTAACAAGCAAGAACCTCAGGAAATTCT-TGGAAACAATTA-CTT--A--TA-

X 339-398   CATCGCGCATCTCTAGATGGAGGAAAGTTTTAGAAGGGACCGTTGAAAGGCCTCCAGAGA
Y 348-404   -ATCACTCATCTCTAGATGGA--AAATTTTTGGAAGGGACCTTTGAAAGGCCTCCAGAAA

X 399-458   AAGTGCTCGAACAGCTTAGGCAAATACTACAAAAATGCCAATTTTCTCTAAAACCGAATT
Y 405-464   AAGTGCTCAATCAG-TCTTT-AAGTACTACAAAAATGCCAGTTTTCTCTAAAACCAAATT

X 459-492   TCTAACGAGTGTCGAACTCTCTT-CCTGCGCTCGA
Y 465-680   TCTGACAAGTATCTAACTCTCTTTC-TGCTCAGAAAACCCCCGGGCTATCATTCTTCAGA
            GTAAGATTTCAGTGTTAGGAATTTCCTTCCTGAACTATTTATTTGTCAGTCACCTGCTAA
            GCAGATGACTTCCTATTGGTTGTCCAGAATGCATGTGGGTATAGTTTACATTCAAATGTA
            CCAAGGGATAGGGGAATGTGGTAACTGAGAGACAGACAC
```

```
X   1-60     ATGGGGACCTGGATTTTGTTTGCCTGCCTCCTGGGAGCAGCCTTTGCTATGCCTGGTGAGT
Y   1-60     ATGGGGACCTGGATTTTGTTTGCCTGCCTCCTGGGAGCAGCCTTTCAGTATGCCTGGTGAGT

X   61-117   AAAATACCCCTGCATAATATTCAATTTCACAAGCTTGGAAATAAAAGTCTGCC--CG-AC-
Y   61-114   AAAAT------TTCG-AATTTCCAATTTCACAAGCTTGGAAATAAAAATCTGCCTCAGATT

X   118-171  ---AGTT-GG-T-AAACTTAAGGGTTTAAGAACAGATCTTGATGTCCTCAAATGTG
Y   115-174  TTTATTTAGGTTAAATTTAAGGGTTTAAGAACAGATCTTGATGTTCAACAAATGTG

X   172-223  TCTGTGTTTAAGAAACACTGGAAGAGCTTG-TTATAA-A----AAAA-AATAT-ATTCC
Y   175-234  ACTGTGTTTAAGAAACATTTTTAAATCTTGATCACAAGATTTTAAAACAAAAACATTCT

X   224-282  CAGATGCCTCCACCCA-AGACTGATTCAGTAGAGCCTGTGCCAGGACT
Y   235-294  CAGTTGCCTTCACCCATATTCTGATTCAGTATAGCCAGAGTGCTGAGAACT

X   283-338  CTGCATTTTAACAAGCA----CCTCAGGAGATTCTGTGGACACAATTAACTTGTAAATAT
Y   295-347  CTGAATTTTAACAAGAACCTCAGGAATTCT-TGGAAACAATTA-CTT--A--TA-

X   339-398  CATCGCCCATCTCTAGATGGAGGAAACTTTTTAGAAGGACCCTTGAAAGGCCTCCAGAGA
Y   348-404  -ATCACACTCATCTCTAGATGGA---AAATTTTTGGAAGGGACCTTGAAAGGCCTCCAGAAA

X   399-458  AAGTGCTCGAACAGCTTAGGCAAATACTACAAAAATGCCATTTTCTCTAAAACCAATT
Y   405-464  AAGTGCTCAATCATCTAACTCTCTTTC-TGCTAGAGTTTTCTCTAAAACCAAATT

X   459-492  TCTAACGAGTGTCGAACTCTCTT-CCTGCCTCGA
Y   465-680  TCTGACAAGTAGTATCTAACTCTCTTTC-TGCTAGAAAACCCCCGGCTATCATTCTTCAGA
             GTAAGATTCAGTGTTAGGAATTCCTTCCTGAACTATTATTGTCAGTCACCTGCTAA
             GCAGATGACTTCCTATTGGTTGTCCAGAATGCATGTGGGTATAGTTTACATTCAAATGTA
             CCAAGGGATAGGGAATGTGGTAACTGAGAGACAGACAC
```

FIG. 5

COMPOSITIONS AND METHODS FOR DETERMINING CANINE GENDER

CROSS REFERENCE TO RELATED APPLICATION

This application claims the benefit of priority under 35 U.S.C. § 119(e) of U.S. Ser. No. 60/439,188, filed Jan. 10, 2003, the entire content of which is incorporated herein by reference.

BACKGROUND OF THE INVENTION

1. Field of the Invention

The invention relates generally to genetic analysis and more specifically to genetic analysis related to canine gender.

2. Background Information

DNA-based techniques have become accepted methods for the determination of gender. The use of DNA for gender determination has been particularly effective in situations where sex is difficult to determine accurately by visual or manual examination, such as in certain avian species, and in circumstances where visual inspection is not possible, and gender must be determined from a biological sample alone.

For example, Griffiths, et al. (1996), U.S. Pat. No. 5,508,165 (Halverson et al. '165), U.S. Pat. No. 5,679,514 (Baker), and U.S. Pat. No. 5,707,809 (Halverson et al. '809) disclose methods for determining the sex of many avian species by DNA techniques. These methods amplify fragments specific to avian sex chromosomes. In some other species, chromosomal regions corresponding to the amelogenin gene have been used to develop DNA-based sexing tests. Amelogenin is involved in the production of tooth enamel and in many mammals there exists a copy of the gene on the X chromosome (AMELX) and another on the Y chromosome (AMELY). Differences in these homologs have allowed the development of gender tests in which different sized fragments are simultaneously amplified from X and Y chromosomes using a single set of primers. These tests have been developed for human (Sullivan et al. 1993), equine (Hasegawa et al. 2000) and bovine DNA (Chen et al. 1999). Although in some cases these primers are not 100% specific to the species being sex-typed and will amplify fragments from other species (Buel et al. 1995), they are unique enough to be only useful as gender markers for the species for which they are developed. The markers developed for human gender testing, for example, do not distinguish male and female canines.

The gender determination of an individual dog using DNA-based techniques would be an important quality control step in applications that utilize canine genotyping. Most canine registries request that information about an individual dog, including gender, be provided by the owner upon registration. In some cases DNA samples, in the form of cheek swabs, are also provided for identity determination or parentage verification. Since the individual dog is not available for visual inspection, the determination of gender from DNA isolated from the submitted sample would verify accuracy of the submitted gender information by the registrant, and improves the integrity of data that becomes part of the registry database.

SUMMARY OF THE INVENTION

The present invention provides a method to determine gender of a canine subject, that includes contacting a nucleic acid sample from the canine subject with at least one probe or primer specific for canine amelogenin, and using the binding of the at least one probe or primer to detect a difference between the canine amelogenin gene on the Y chromosome and the canine amelogenin gene on the X chromosome, thereby determining gender of the canine subject. In certain aspects, binding of the at least one probe or primer is detected. For example, gender of the canine subject can be determined by contacting the nucleic acid sample with at least one probe or primer that specifically binds SEQ ID NO:22 and/or SEQ ID NO:23.

In certain aspects, gender of the canine subject is determined by contacting the nucleic acid sample with at least one probe or primer that specifically binds SEQ ID NO:10 (Canine X amelogenin sequences 1-143 (Table 3)) and/or SEQ ID NO:11. (Canine Y amelogenin sequences 1-146 (Table 3)). For example, a first primer of a primer pair specifically binds to SEQ ID NO:6 (Canine X amelogenin sequences 1-76 (Table 3)) and/or SEQ ID NO:7 (Canine Y amelogenin sequences 1-70 (Table 3)), and a second primer of the primer pair specifically binds to SEQ ID NO:8 (Canine X amelogenin sequences 77-143 (Table 3)) and/or SEQ ID NO:9 (Canine Y amelogenin sequences 71-146 (Table 3)). In certain aspects, the first primer is SEQ ID NO:3 or SEQ ID NO:4, and the second primer is SEQ ID NO:5.

In certain aspects and embodiments disclosed herein, in addition to detecting binding of at least one probe or primer to a canine amelogenin gene, methods of the present invention include detecting binding of at least one probe or primer to a canine microsatellite locus, to provide genotype and gender information.

BRIEF DESCRIPTION OF THE DRAWINGS

FIG. 5 provides a comparison of consensus sequences of canine X (SEQ ID NO:22) and Y (SEQ ID NO:23) partial amelogenin sequences. The shaded sequences and gaps indicate differences between the canine AMELX and AMELY sequences.

DETAILED DESCRIPTION OF THE INVENTION

Figure 1:
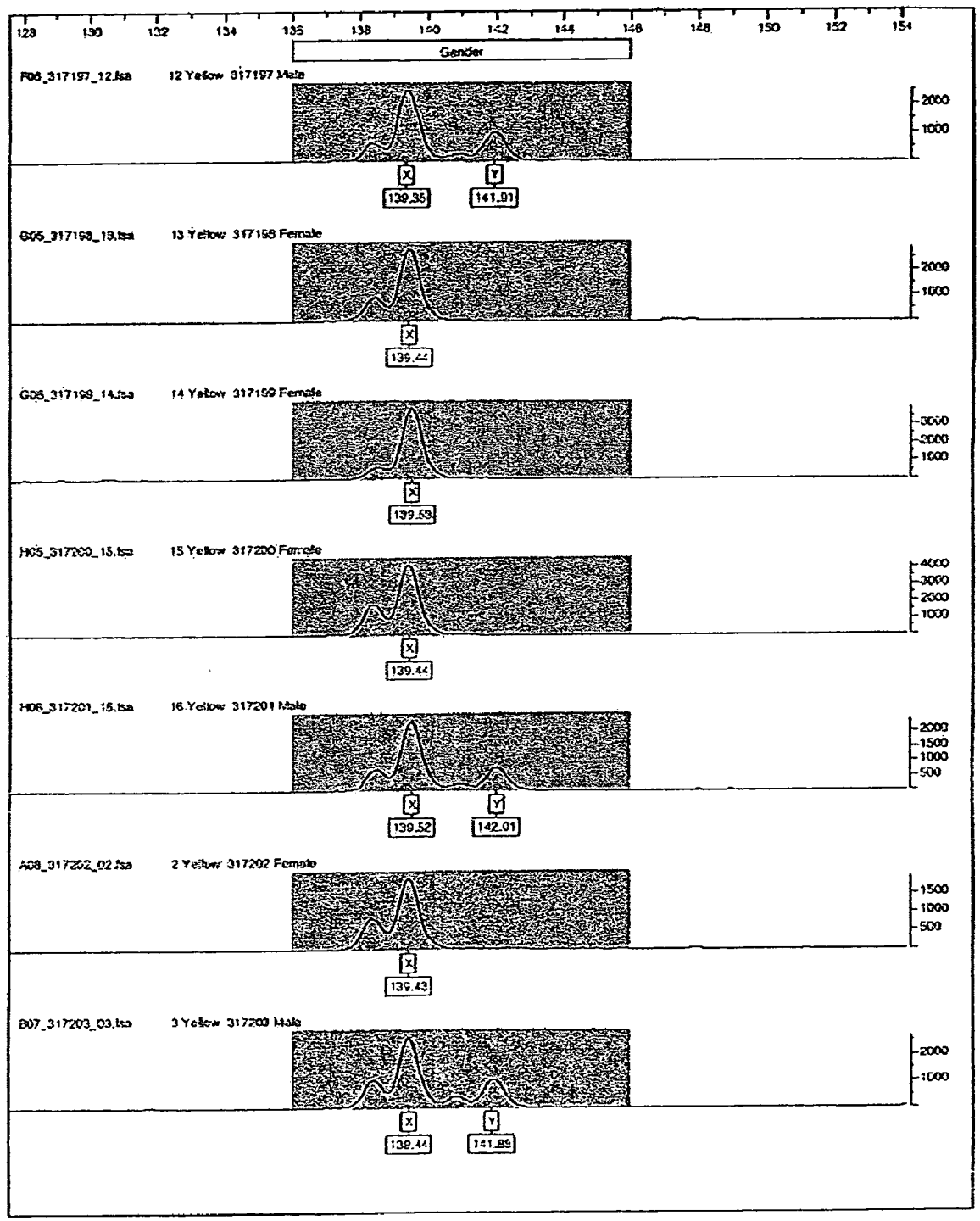
FIG. 1 illustrates determination of gender in canine samples by the analysis of nucleic acid products derived from the use of canine amelogenin specific primers. The plots, generated using an ABI Prism, shows X and Y specific amplification products for various canine samples, generated using BFK90059 and BFK90065. The X axis is scan number and the Y axis is relative intensity of signal.
Figure 1:
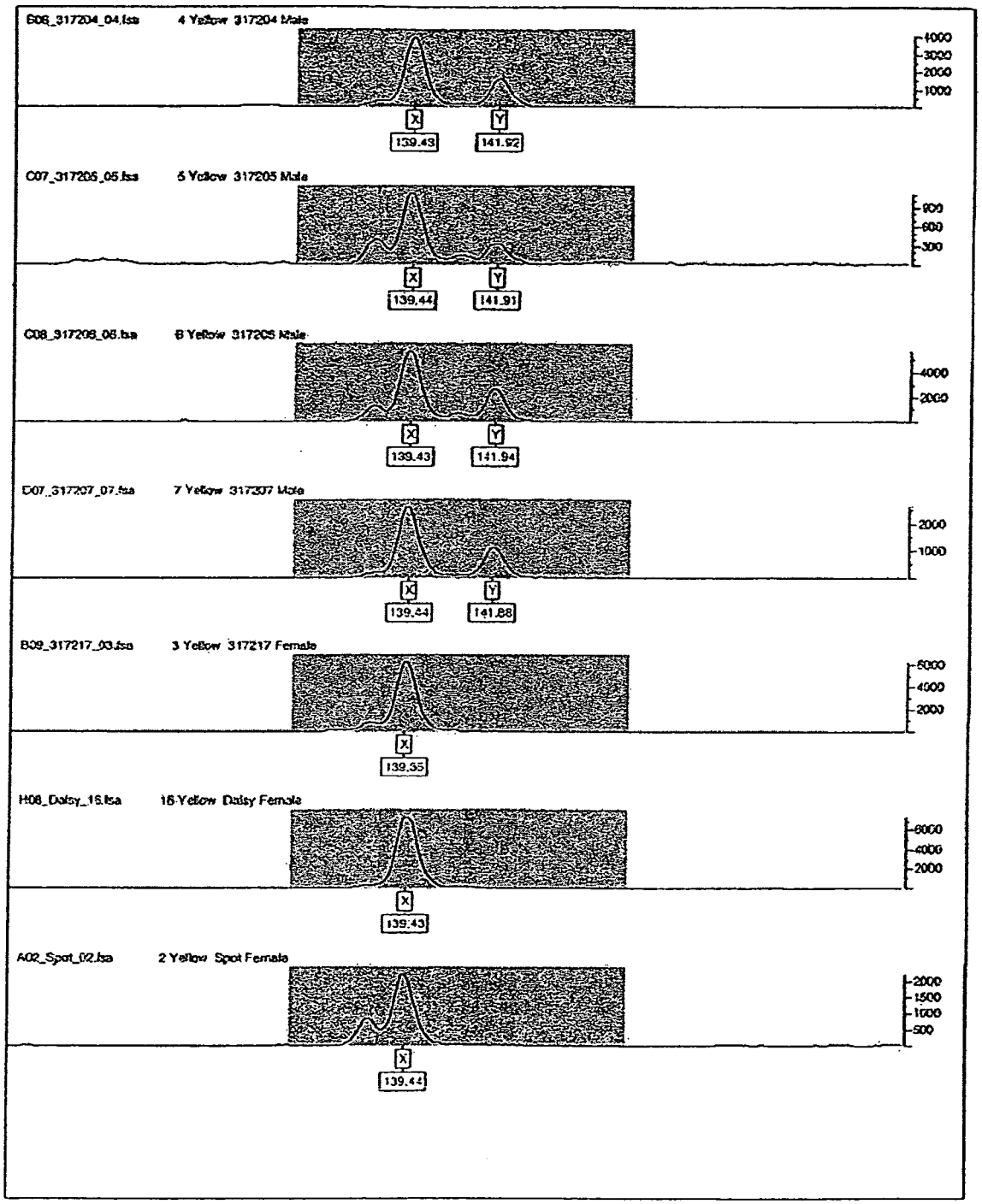

The present invention is based on the discovery of differences in the canine amelogenin gene homologs on the X (AMELX) and Y (AMELY) chromosomes. Furthermore, the present invention is based on the design and identification of PCR primers that specifically amplify regions on both canine sex chromosomes and accurately distinguish them, thereby providing amplification products that are canine gender markers. The PCR primers can be used in multiplexing genotyping assays. The primers that were identified to amplify and distinguish canine sex chromosomes were designed so that they do not amplify human DNA, a possible source of contamination in canine genotyping analysis. Therefore, these primers are useful as quality control standards in canine genotyping reactions, to assure that amplification products are generated from canine template polynucleotides and not polynucleotides from a technician.

Canine gender determination is an important component of canine parentage and identity testing and provides quality assurance when used in conjunction with DNA-based parentage and identity testing. The results of canine gender determination are used by breed registries in creating pedigrees for specific animals. These data are added to breed registry databases and thereby become a component of an animal's official pedigree. Further, results can be used in forensic cases involving canines, whereby results could be used to "include or exclude" specific animals in a manner similar to human forensic genotyping practices. The gender markers can also serve as stand alone markers, or as part of a set of standard markers for comparison of genotypes.

Accordingly, provided herein is a method to determine gender of a canine subject, that includes contacting a nucleic acid sample from the canine subject with at least one probe or primer specific for canine amelogenin, and detecting binding of the at least one probe or primer, thereby determining gender of the canine subject. Binding of the at least one probe or primer distinguishes the canine amelogenin gene on the X chromosome from the amelogenin gene on the Y chromosome. The presence of a copy of the amelogenin gene on the Y chromosome indicates that the subject is male, whereas the absence of a copy of the amelogenin gene on the Y chromosome indicates that the subject is female, thereby providing a determination of the gender of the canine subject.

In certain aspects, gender of the canine subject is determined by contacting the nucleic acid sample with at least one probe or primer that specifically binds SEQ ID NO:22, a region of the canine amelogenin gene on the X chromosome, and/or SEQ ID NO:23, a corresponding region of the canine amelogenin gene on the Y chromosome, and which are effective at allowing differences between the sequence of SEQ ID NO:22 and/or SEQ ID NO:23 to be identified.

The probe or primers specific for the canine amelogenin gene are designed so that they can be used to detect differences disclosed herein between the canine amelogenin gene on the X chromosome and the canine amelogenin gene on the Y chromosome. These differences are apparent, for example, from a comparison of SEQ ID NO:20, the nucleotide sequence of a region of the canine amelogenin gene on the X chromosome, and SEQ ID NO:21, the nucleotide sequence of the corresponding region of the canine amelogenin gene on the Y chromosome. It will be understood based on the differences in these sequences, that probes and primers can be designed that only recognize the X or Y version, or that can be used to generate a product that is detectably distinguishable between the X and Y version of the gene. FIG. 5 provides a comparison of larger partial sequences of the X (SEQ ID NO:22) and Y (SEQ ID NO:23) copies of the amelogenin gene. It will be understood that based on the present disclosure, specific assays can be devised that exploit the differences in the X and Y chromosome versions of the canine amelogenin gene, for example the partial sequences of the X and Y chromosome versions of the amelogenin gene provided in SEQ ID NOS:22 and 23.

Furthermore, it will also be understood that the sequence of the entire canine (e.g. dog) amelogenin gene can be identified and characterized using standard methods based on the present disclosure, combined with known sequences of the amelogenin gene in other species, for example the human amelogenin gene sequence data (Genbank accession numbers AY0040206 (genomic) and M86932 (mRNA) (*Homo sapiens* amelogenin X (AMELX)); and Genbank accession numbers AC013412 (genomic (Bac clone RP11-507A3)) and M86933(mRNA)(*Homo sapiens* amelogenin Y (AMELY)), and dog genomic data (The Dog Genome: Survey Sequencing and Comparative Analysis, Kirkness et al. (2003) *Science*, Vol 301 1898-1903, incorporated by reference herein in its entirety (Genbank accession numbers AACN01000001-AACN011089636 and CE000001-CE853796)). Additional regions of the canine amelogenin gene are likely to be identified from the complete canine amelogenin gene sequence that include nucleotide sequence differences between the copy of the gene on the X chromosome and that on the Y chromosome. These additional regions can be utilized to design additional probes and primers that can be used in the methods disclosed herein, in place of, or in combination with, the probes and primers disclosed herein. Furthermore, based on the present disclosure, it will be understood that it is likely that other canine genes that are found on both the X and Y chromosomes will include X or Y chromosome-specific differences that can be exploited in methods to determine canine gender, for example the Y chromosome SRY gene and the X homologue SOX3, and in the ZFY and ZFX genes (Griffiths, R. (2000) Sex identification using DNA markers; In: Molecular methods in ecology (Ed. by Baker A J) Blackwell Science, London).

A method of the present invention to determine gender of a canine subject, can include contacting a nucleic acid sample from the canine subject with at least one probe or primer specific for a canine amelogenin gene, and detecting binding of the at least one probe or primer to a target region of the canine amelogenin gene and/or detecting an extension product of the canine amelogenin gene generated from the at least one primer. A difference in the binding of the at least one probe or primer, or a difference in the extension product of the at least one probe or primer, distinguishes the copy of the canine amelogenin gene on the X chromosome from the copy of the canine amelogenin gene on the Y chromosome. The presence of a copy of the amelogenin gene on the Y chromosome indicates that the subject is male, whereas the absence of a copy of the amelogenin gene on the Y chromosome indicates that the subject is female, thereby providing a determination of the gender of the canine subject. The target region is close enough to a nucleotide(s) that is different between amelogenin gene on the X chromosome and the amelogenin gene on the Y chromosome, such that binding of the probe or primer can be used to detect the difference between the amelogenin gene on the X chromosome from the amelogenin gene on the Y chromosome. For example, the target region can be within 1000, 500, 250, 150, 100, 50, 25, 20, 15, 10, 5, 4, 3, 2, or 1 nucleotide of a nucleotide position that is different between the amelogenin gene on the X chromosome and the amelogenin gene on the Y chromosome.

A method to determine gender of a canine subject of the present invention, can include contacting a nucleic acid sample from the canine subject with at least one probe or primer specific for canine amelogenin, and detecting a canine amelogenin gene on a Y chromosome based on binding of the probe or primer. The presence of a copy of the amelogenin gene on the Y chromosome indicates that the subject is male, whereas the absence of a copy of the amelogenin gene on the Y chromosome indicates that the subject is female, thereby providing a determination of the gender of the canine subject. In certain aspects, the methods involve detecting both the canine amelogenin gene X chromosome copy and the canine amelogenin gene Y chromosome copy to determine gender of the canine subject.

In another related embodiment, the present invention provides a method to determine gender of a canine subject, wherein a nucleic acid sample from the canine subject is contacted with at least one probe or primer specific for canine amelogenin, and the binding of the at least one probe or primer is used to detect a difference in the canine amelogenin copy on the Y chromosome and the canine amelogenin copy on the X chromosome, thereby determining gender of the canine subject.

In general, methods of the present invention determine whether a subject is male or female (i.e. determine the gender of a canine subject) by attempting to detect the presence of a copy of the amelogenin gene on the Y chromosome, which indicates that the subject is male. Conversely, the absence of a copy of the amelogenin gene on the Y chromosome indicates that the subject is female. The method can also include detecting a copy of the amelogenin gene on the X chromosome. The detection of a copy of the amelogenin gene on the X chromosome, but not the amelogenin gene on the Y chromosome, is determinative of a female subject. The detection of a copy of the amelogenin gene on the X chromosome and a copy of the amelogenin gene on the Y chromosome, is determinative of a male subject. The detection of the presence of the amelogenin gene on the X chromosome, in addition to providing gender information, provides further assurance that an assay was successful. In certain aspects, as indicated herein, the method detects only the presence of the amelogenin gene on the Y chromosome.

In certain aspects of methods disclosed herein, binding of at least one probe or primer is detected and used to determine gender of the canine subject by determining the size of an amplification product(s) generated using the primer or primer pair, or by determining the size of a restriction fragment(s) generated from a sample and identified using the probe. For example, probes and/or primers can be used to synthesize or detect a nucleic acid product that is different between the canine amelogenin gene copy on the X chromosome and the canine amelogenin gene copy on the Y chromosome. The nucleic acid can be, for example, a primer extension product (e.g. a sequencing reaction product), an amplification product, or a restriction enzyme cleavage product. As illustrated in FIG. 1, methods disclosed herein can detect the presence or absence of the Y chromosome by detecting the presence or absence an amplification product that is detectably distinguishable depending on whether it is generated from the Y chromosome or the X chromosome.

It will be understood based on the present disclosure that other methods can be used to exploit the canine sequence information provided herein to distinguish the X from the Y chromosome copy of the amelogenin gene. These methods include, but are not limited to, polynucleotide sequencing, primer extension, differential hybridization, oligo ligation assay (OLA), mass spectroscopy or a SNP detection method, of which many are known in the art.

In certain aspects, gender of the canine subject is determined by contacting the nucleic acid sample with at least one probe or primer that specifically binds SEQ ID NO:10 (Canine X amelogenin sequences 1-143 (Table 3)) and/or SEQ ID NO:11. (Canine Y amelogenin sequences 1-146 (Table 3)). For example, at least one probe or primer can specifically bind to SEQ ID NO:6 (Canine X amelogenin sequences 1-76 (Table 3)) and/or SEQ ID NO:7 (Canine Y amelogenin sequences 1-70 (Table 3)), and at least one other probe or primer can specifically bind to SEQ ID NO:8 (Canine X amelogenin sequences 77-143 (Table 3)) and/or SEQ ID NO:9 (Canine Y amelogenin sequences 71-146 (Table 3)). Such methods take advantage of the X or Y chromosome-specific insertions and/or deletions between SEQ ID NO:10 and SEQ ID NO:11.

In certain aspects, a primer pair is employed in the methods for determining canine gender. In fact, primer pairs used in such methods represent another embodiment of the invention. In methods disclosed herein that employ a primer pair, typically the first primer and the second primer bind opposite strands of a target polynucleotide and prime polynucleotide synthesis from the target polynucleotide in opposite directions. Typically, the primer pairs are used in an amplification reaction, as are known in the art and disclosed in more detail herein. In certain embodiments, the present invention provides an isolated primer pair that primes polynucleotide synthesis of the canine amelogenin gene across a region that includes an X or Y chromosome-specific insertion or deletion.

Accordingly, in these aspects gender of the canine subject is determined by contacting the nucleic acid sample with a primer pair. Target sequences for binding of primers of the primer pair can be sequences that are at least 80%, 85%, 90%, 95%, 99%, or 100% identical between the canine X and Y amelogenin genes and bind (i.e. hybridize) to target regions of the canine amelogenin gene that flank insertion/deletion areas. These primer pairs are designed to produce amplification fragments of different sizes for the X and Y chromosomes. In certain aspects, one primer of the primer pair is labeled. Detectable labeling of a polynucleotide or oligonucleotide such as a primer, is well known in the art, as discussed in more detail herein. In certain aspects, for example, a probe or primer is fluorescently labeled.

In certain examples, a first primer of the primer pair specifically binds to SEQ ID NO:6 and/or SEQ ID NO:7 and a second primer of the primer pair specifically binds to SEQ ID NO:8 and/or SEQ ID NO:9. A specific illustration of this is provided in the Example provided herein. One set of primers (BFK90052 (SEQ ID NO:5) and BFK90055 (SEQ ID NO:3) produces a 143 base band in male and female canine samples and an extra band of 146 bases in male samples. Another set of primers, SEQ ID NO:5 and SEQ ID NO:4 produces a 139 base band in male and female canine samples and an extra band of 142 bases in male samples. It will be understood that other regions of the amelogenin gene that flank the region of the gene identified in Table 3 (SEQ ID NO:10 and SEQ ID NO:11) can be used as binding regions for a primer pair to amplify across this region, which includes insertions and deletion differences between the canine X and canine Y chromosomes.

Furthermore, typically the primer pairs used in the methods of the present invention generate different sized amplification products in canines than in humans, or generate lower levels or no amplification products with human samples. For example, as illustrated in the Example, when human DNA was tested using primers BFK90065 (SEQ ID NO:4) and BFK90059 (SEQ ID NO:5), a faint 143 base band was detected in female and male but no 146 base band was detected in any human sample, thus eliminating any concern of human DNA contamination. These results were expected since BFK90065 is in a highly conserved region near the initial amelogenin ATG start codon, whereas BFK90059 lies within an intron and has 19/22 bases identical to human amelogenin-X but only 15/22 bases identical to human amelogenin-Y with the 3' end of the primer being most different (Table 1).

In certain aspects, the first primer includes at least 5, 6, 7, 8, 9, 10, 11, 12, 13, 14, 15, 16, 17, 18, 19, 20, 21 or 22 contiguous nucleotides of SEQ ID NO:3, and the second primer includes at least 5, 6, 7, 8, 9, 10, 11, 12, 13, 14, 15, 16, 17, 18, 19, 20, 21 or 22 contiguous nucleotides of SEQ ID NO:5. In another aspect, the first primer includes at least 5, 6, 7, 8, 9, 10, 11, 12, 13, 14, 15, 16, 17, or 18 contiguous nucleotides of SEQ ID NO:4, and the second primer includes at least 5, 6, 7, 8, 9, 10, 11, 12, 13, 14, 15, 16, 17, 18, 19, 20, 21 or 22 contiguous nucleotides of SEQ ID NO:5. In another aspect, the first primer is at least 90%, 95%, 96%, 97%, 98%, or 99% identical to SEQ ID NO:3 or SEQ ID NO:4, and the second primer is at least 90%, 95%, 96%, 97%, 98%, or 99% identical to SEQ ID NO:5.

The exact composition of the primer or probe sequences of the present methods are not critical to the invention, but they must hybridize to sequences of the canine amelogenin gene under moderate or high stringency conditions (i.e. specifically bind), or for probes or primers to microsatellite sequences, they must hybridize under moderate or high stringency conditions to U and/or U' sequences that flank repeats of the microsatellites, as disclosed herein. Therefore, a probe or primer that is specific for a canine amelogenin gene, binds to the canine amelogenin gene under moderate or high stringency conditions. Furthermore, a probe or primer that is specific for a canine amelogenin gene is identified such that they are useful for performing the methods disclosed herein. For example, when a primer pair that is specific for a canine amelogenin gene is used to amplify a region of the canine amelogenin gene, an amplification product is generated that is a unique size from any other detectable amplification products generated using the primer pair to amplify canine (e.g. dog) genomic DNA. To maximize the resolution of size differences between products generated from the amelogenin gene on the X and Y chromosome or from a microsatellite locus, it is preferable to choose a primer sequence that is close to an insertion or deletion sequence for the amelogenin gene, or close to the repeat sequence for the microsatellites. Thus, primers usually bind within at least about 100 nucleotides, 50 nucleotides, or 25 nucleotides of an insertion, deletion, or repeat.

Algorithms for the selection of primer sequences are generally known and are available in commercial software packages. Primers can be designed to be used in primer extension reactions. Primer pairs of the present invention can be designed to hybridize to complementary strands of chromosomal DNA, and prime towards an insertion, deletion, or repeat sequences, so that these sequences are amplified to produce a product of a detectably different length between individuals and/or for the X and Y chromosome. Primers will usually be at least about 5, 6, 7, 8, 9, 10, 11, 12, 13, 14, 15, 16, 17, or 18 nucleotides in length, and usually not more than about 50, 45, 40, 35, 30, or 25 nucleotides in length.

It will be recognized that some amount of non-specific hybridization is unavoidable, but is acceptable provided that hybridization to a target nucleotide sequence is sufficiently selective such that it can be distinguished over the non-specific cross-hybridization, for example, at least about 2-fold more selective, generally at least about 3-fold more selective, usually at least about 5-fold more selective, and particularly at least about 10-fold more selective, as determined, for example, by an amount of labeled oligonucleotide that binds to target nucleic acid molecule as compared to a nucleic acid molecule other than the target molecule, particularly a substantially similar (i.e., homologous) nucleic acid molecule other than the target nucleic acid molecule. Conditions that allow for selective hybridization can be determined empirically, or can be estimated based, for example, on the relative GC:AT content of the hybridizing oligonucleotide and the sequence to which it is to hybridize, the length of the hybridizing oligonucleotide, and the number, if any, of mismatches between the oligonucleotide and sequence to which it is to hybridize (see, for example, Sambrook et al., "Molecular Cloning: A laboratory manual (Cold Spring Harbor Laboratory Press 1989)).

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

The term "polynucleotide" is used broadly herein to mean a sequence of deoxyribonucleotides or ribonucleotides that are linked together by a phosphodiester bond. For convenience, the term "oligonucleotide" is used herein to refer to a polynucleotide that is used as a primer or a probe.

An oligonucleotide or polynucleotide can be RNA or can be DNA, which can be genomic DNA, a gene or a portion thereof, a cDNA, a synthetic polydeoxyribonucleic acid sequence, or the like, and can be single stranded or double stranded, as well as a DNA/RNA hybrid. In various embodiments, a polynucleotide, including an oligonucleotide (e.g., a probe or a primer) can contain nucleoside or nucleotide analogs, or a backbone bond other than a phosphodiester bond. In general, the nucleotides comprising a polynucleotide or oligonucleotide are naturally occurring deoxyribonucleotides, such as adenine, cytosine, guanine or thymine linked to 2'-deoxyribose, or ribonucleotides such as adenine, cytosine, guanine or uracil linked to ribose. However, a polynucleotide or oligonucleotide also can contain nucleotide analogs, including non-naturally occurring synthetic nucleotides or modified naturally occurring nucleotides. Such nucleotide analogs are well known in the art and commercially available, as are polynucleotides containing such nucleotide analogs (Lin et al., *Nucleic Acids Research* (1994) 22:5220-5234 Jellinek et al., *Biochemistry* (1995) 34:11363-11372; Pagratis et al., *Nature Biotechnol.* (1997) 15:68-73, each of which is incorporated herein by reference). Oligonucleotides, such as primers and probes, can also be comprised of peptide nucleic acids (PNA) (Nielsen PE and Egholm M. (1999) *Curr. Issues Mol. Biol.* 1:89-104).

The covalent bond linking the nucleotides of an oligonucleotide or polynucleotide generally is a phosphodiester bond. However, the covalent bond also can be any of numerous other bonds, including a thiodiester bond, a phosphorothioate bond, a peptide-like bond or any other bond known to those in the art as useful for linking nucleotides to produce synthetic polynucleotides (see, for example, Tam et al., *Nucl. Acids Res.* (1994) 22:977-986, Ecker and Crooke, *BioTechnology* (1995) 13:351360, each of which is incorporated herein by reference). The incorporation of non-naturally occurring nucleotide analogs or bonds linking the nucleotides or analogs can be particularly useful where the oligonucleotide or polynucleotide is to be exposed to an environment that can contain a nucleolytic activity, including, for example, a tissue culture medium or upon administration to a living subject, since the modified polynucleotides can be less susceptible to degradation.

A polynucleotide or oligonucleotide that includes naturally occurring nucleotides and phosphodiester bonds can be chemically synthesized or can be produced using recombinant DNA methods, using an appropriate polynucleotide as a template. In comparison, a polynucleotide or oligonucleotide comprising nucleotide analogs or covalent bonds other than phosphodiester bonds generally are chemically synthesized, although an enzyme such as T7 polymerase can incorporate certain types of nucleotide analogs into a polynucleotide and, therefore, can be used to produce such a polynucleotide recombinantly from an appropriate template (Jellinek et al., supra, 1995). Thus, the term polynucleotide as used herein includes naturally occurring nucleic acid molecules, which can be isolated from a cell, as well as synthetic molecules, which can be prepared, for example, by methods of chemical synthesis or by enzymatic methods such as by the polymerase chain reaction (PCR).

A method of the present invention can be performed using a specific binding pair member to a canine gender maker. As used herein, the term "specific binding pair member" refers to a molecule that specifically binds or selectively hybridizes to another member of a specific binding pair. Specific binding pair member include, for example, probes, primers, polynucleotides, antibodies, etc. For example, a specific binding pair member includes a primer or a probe that selectively hybridizes to a target polynucleotide that includes an amelogenin gene, or that specifically hybridizes to an amplification product generated using the target polynucleotide as a template.

In certain aspects, a probe is employed in the methods for determining canine gender of the present invention. Accordingly, in these aspects gender of the canine subject is determined by contacting the nucleic acid sample with a probe that specifically binds a target sequence. The probe is typically labeled, for example fluorescently labeled. Target sequences for binding of primers of the primer pair can include, for example, sequences within the canine amelogenin genes that include insertion/deletion areas, with the aim of obtaining differential binding of the probe to the X and Y chromosomes. For example, a probe can be designed to bind to a target region that includes nucleotides 55 to 59 of the canine amelogenin gene present on the X chromosome (i.e. nucleotides 55 to 59 of SEQ ID NO:14 and SEQ ID NO:22), such that the probes do not bind to a corresponding target region of the amelogenin gene on the Y chromosome.

As used herein, the term "at least one", when used in reference to a primer, probe, microsatellite, or the like, means 1, 2, 3, 4, 5, 6, 7, 8, 9, 10, etc. Reference to "at least a second" primer, probe, microsatellite, or the like, means two or more, i.e., 2, 3, 4, 5, 6, 7, 8, 9, 10, etc., primers probes, microsatellites, or the like.

As used herein, the term "infer" or "inferring", when used in reference to gender, means drawing a conclusion about gender using a process of analyzing individually or in combination, amplification products or probe-bound polynucleotides generated from a nucleic acid sample of the subject, using a method disclosed herein, and comparing the amplification products or probe-bound polynucleotides to known gender makers. Typically, for methods of the invention, a qualitative analysis, such as identifying whether 1 or 2 amplification products are produced, is sufficient to infer the gender of the subject.

A canine subject analyzed using the methods disclosed herein is a member of the family Canidae, which includes the species dogs, wolves, coyotes, foxes and jackals. The degree of homology between these species is high, and the subject methods are expected to be effective with any canine species. Furthermore, as illustrated herein, the methods have accurately determined gender of a subject in a wide range of dog breeds, including many common breeds of dogs. The nucleic acid from the canine subject is typically a genomic DNA sample that is isolated from the subject or subjects that are to be tested. DNA can be isolated from any nucleated cellular source such as blood, hair shafts, saliva, mucous, biopsy, or feces. Amplification can be performed on the DNA from a single cell, although it is convenient to use at least about $10^5$ cells.

Typically, primers of the present invention are used to amplify a region of genomic DNA that includes an insertion or deletion that is present in the X or Y chromosome, but not both the X and Y chromosome. The amplification reaction can be, as non-limiting examples, the polymerase chain reaction or the ligase chain reaction. Suitable reaction conditions for PCR are described, for example, in Saiki, et al. (1985) *Science* 239:487, and Sambrook, et al. Molecular Cloning: A Laboratory Manual, CSH Press 1989, pp.14.2-14.33. Useful thermostable polymerases known in the art include those isolated, for example, from *Thermus aquaticus, Thermococcus litoralis, Pyrococcus furiosis*, and *Thermus thermophilus*, as is known. A discussion of the ligase chain reaction (LCR) may be found in International patent application WO 9302215.

Conveniently, a probe or primer of the present invention can include a detectable label. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N', N'-tetramethyl-6-carboxyrhodamine (TAMRA), radioactive labels, e.g. $^{32}P$, $^{35}S$, or $^{3}H$. The label can be a two stage system, where the amplified DNA is conjugated to biotin or haptens, for example, that have a high affinity binding partner, for example avidin or specific antibodies, where the binding partner is conjugated to a detectable label. The label can be conjugated to one or both of the primers. Alternatively, the pool of nucleotides used in the amplification can be labeled, so as to incorporate the label into the amplification product.

After amplification, the products can be size fractionated. Fractionation can be performed, for example, by gel electrophoresis, such as denaturing acrylamide or agarose gels. A convenient system uses denaturing polyacrylamide gels in combination with an automated DNA sequencer, see Hunkapillar et al. (1991) *Science* 254:59-74. The automated sequencer is particularly useful with multiplex amplification. Capillary electrophoresis can also be used for fractionation. A review of capillary electrophoresis can be found in Landers, et al. (1993) *BioTechniques* 14:98-111.

In one aspect, reaction and PCR conditions for a method to determine gender provided herein, include the following: 0.29 pmoles of each of BFK90059 and BFK90065 primers, 1.5× Taq Gold Buffer, 2.5 mM $MgCl_2$, 0.175 mM each dNTP and 0.75 units of AmpliTaq Gold Polymerase in an 5 μl reaction containing a highly variable amount of canine DNA (approximately 0.5-100 ng). PCR: 95° C. for 12 minutes, 15 cycles of 30 seconds at 94° C., 30 seconds at 64° C. decreasing 0.2° C./cycle to 61° C., and 1 minute at 72° C., followed by 20 cycles of 30 seconds at 94° C., 30 seconds at 61° C., and 1 minute at 72° C., followed by a final extension of 72° C. for 45 minutes in a Perkin Elmer 9600 thermocycler.

In another embodiment, the present invention provides an isolated oligonucleotide that can be used as a primer or probe in the methods disclosed herein. For example, in one aspect, the oligonucleotide binds to SEQ ID NO:10 and/or SEQ ID NO:11, wherein the oligonucleotide is between 10 and 50 nucleotides in length. The oligonucleotide can be, for example, 10, 11, 12, 13, 14, 15, 16, 17, 18, 19, 20, 21, 22, 23, 24, 25, 30, 35, 40, 45, or 50 nucleotides in length.

In certain aspects, the oligonucleotide includes at least 10, 11, 12, 13, 14, 15, 16, 17, or 18 contiguous nucleotides of at least one of SEQ ID NOS:1 to 5. In fact, in specific examples of the invention, the oligonucleotide is any one of SEQ ID NOS:1 to 5. Furthermore, the oligonucleotide can include a detectable label.

In certain embodiments pairs of oligonucleotides disclosed herein form primer pairs, which themselves form another embodiment of the present invention, as disclosed in more detail above.

Methods of the present invention for determining gender of a canine subject are useful, for example as a quality control step in applications that utilize canine genotyping. As indicated herein, data provided by the methods can be used to verify gender information provided by to a canine registry. Accordingly, the present invention provides a method for quality control testing of a nucleic acid sample from a canine subject, comprising determining gender of the canine subject using a gender marker, and comparing the determined gender with a reported gender of the canine subject. The reported gender can be gender information provided to a registry. In other aspects, gender information determined using methods herein is compared to known gender information. In these embodiments, the method provides a quality assurance test that an amplification reaction, for example provides valid results.

Furthermore, aspects of the methods of the invention disclosed herein, wherein human samples generate a different amplification product than canine samples, are useful to confirm that an amplification product(s) was generated from nucleic acids from a canine sample and not from contaminating human DNA. In this aspect, the gender determination is performed as a quality control in a genotyping reaction of at least one microsatellite locus, as disclosed in more detail herein. Accordingly, the quality control testing and the genotyping can be performed in the same reaction using multiplex procedures disclosed herein.

In another embodiment, provided herein is a method to detect binding of at least one primer or probe to a canine amelogenin gene, that includes contacting a nucleic acid sample from a canine subject with at least one probe or primer specific for canine amelogenin. Embodiments directed at detecting binding of at least one primer or probe to a canine amelogenin gene are identical to those disclosed above for determining gender, except that the methods in certain aspects, do not include the step of determining gender. These methods are useful, for example, for genotyping methods wherein differences among canine subjects in the amelogenin gene are identified and used to identify the canine subject.

Thus, certain examples of methods for detecting binding of at least one probe or primer to the amelogenin gene are genotyping methods. Accordingly, in certain embodiments, the present invention provides a method to genotype a canine subject, that includes contacting a nucleic acid sample from the canine subject with at least one probe or primer specific for canine amelogenin, and detecting binding of the at least one probe or primer, thereby genotyping the canine subject. These genotyping include probes and primer pairs that specifically bind to nucleotides that are polymorphic and/or probes and primer pairs that provide gender information, as disclosed above.

For example, in certain aspects the nucleic acid sample is contacted with at least one probe or primer that specifically binds SEQ ID NO:22 and/or SEQ ID NO:23. In another example, the at least one probe or primer specifically binds SEQ ID NO:10 and/or SEQ ID NO:11. In another example, the nucleic acid sample is contacted with a primer pair, wherein a first primer of the primer pair specifically binds to SEQ ID NO:6 and/or SEQ ID NO:7 and a second primer of the primer pair specifically binds to SEQ ID NO:8 and/or SEQ ID NO:9.

In certain aspects, for example, the first primer includes at least 5, 6, 7, 8, 9, 10, 11, 12, 13, 14, 15, 16, 17, 18, 19, 20, 21 or 22 contiguous nucleotides of SEQ ID NO:3, and the second primer includes at least 5, 6, 7, 8, 9, 10, 11, 12, 13, 14, 15, 16, 17, 18, 19, 20, 21 or 22 contiguous nucleotides of SEQ ID NO:5. In another aspect, the first primer includes at least 5, 6, 7, 8, 9, 10, 11, 12, 13, 14, 15, 16, 17, or 18 contiguous nucleotides of SEQ ID NO:4, and the second primer includes at least 5, 6, 7, 8, 9, 10, 11, 12, 13, 14, 15, 16, 17, 18, 19, 20, 21 or 22 contiguous nucleotides of SEQ ID NO:5.

As indicated herein, in certain aspects, methods of the present invention are multiplex reactions. Accordingly, "at least one probe or primer" can include, for example 1, 2, 3, 4, 5, 6, 7, 8, 9, 10, 11, 12, 13, 14, 15, 16, 17, 18, 19, 20, 25, 30, 40, 50, 60, 70, 80, 90, 100, or more probes, primers, or combinations thereof. The probes or primers can include probes and primers that specifically hybridize to the amelogenin gene and, in certain aspects, include probes and primers that specifically hybridize to a microsatellite locus (See below). As indicated above, specific hybridization or specific binding is hybridization or binding under stringent hybridization conditions.

In certain aspects and embodiments disclosed herein, in addition to detecting binding of at least one probe or primer to a canine amelogenin gene, methods of the present invention include detecting binding of at least one probe or primer to a canine microsatellite locus. Canine microsatellite loci and methods for genotyping and identifying additional canine microsatellites are disclosed in U.S. Pat. No. 5,874,217, incorporated by reference in its entirety herein.

Microsatellites are perfect, imperfect, or compound arrays of tandemly repeated nucleotide sequences embedded in an otherwise unique nucleotide sequence. Microsatellite repeats typically range from one to six base pairs (bp) in length. The microsatellite repeat arrays vary in the number of repeats from 6 to 30 or more in humans. However, the longer arrays of repeats are less frequently isolated. Microsatellites may consist of simple repeats containing only one uninterrupted repeated sequence, imperfect repeats containing two identical repeats separated by a small interval of non-repeated nucleotides, or compound repeats containing several different repeated sequence types (Weber, 1990). For an individual, any particular microsatellite chromosomal locus may vary in the number of repeats present.

Commonly used methods of genetic mapping by microsatellites take advantage of length variations among individuals (Weber and May, 1989). Utilizing the nucleotide sequence of the cloned microsatellite and its flanking regions, oligonucleotide primers for the PCR are designed that anneal to unique sequences that flank the repeats. The primers can be designed as near or far from the microsatellite as desired, the only limit being the resulting size of the PCR product for subsequent analysis.

Methods for detection and size determination of PCR products from a specific microsatellite locus are known in the art, and can be accomplished, for example using amplification methods discussed herein.

As disclosed in more detail in U.S. Pat. No. 5,874,217, microsatellite loci that are useful in the subject methods will have the general formula:

$U(R)_n U'$, where

U and U' are non-repetitive flanking sequences that uniquely identify the particular locus, R is a repeat motif, and n is the number of repeats, which is variable in a population. The locus will be present on a canine chromosome. Specific examples are provided in the Sequence Listing, SEQ ID NO: 1 through SEQ ID NO:20.

Within the flanking sequences U and U', sequences can be selected for amplification primers, P and P'. Tables 4 through 6 provide examples of microsatellite amplification primers. It will be understood that these primers and probes, as well as the canine amelogenin primers and probes disclosed herein are exemplary, and other primers and probes can be identified using the present disclosure and known methods. The number of repeats at a specific locus, n, are polymorphic in a population, thereby generating individual differences in the length of DNA that lies between U and U'. The number will vary from at least 1 repeat to as many as about 150 repeats.

Methods that detect binding of probes and primers to both the amelogenin gene and to microsatellite loci are typically multiplex reactions, such as multiplex amplification reactions. Multiplex genotyping provide a genetic fingerprint for the identification of the canine. Multiplex amplification may be performed in which several sets of primers are combined in the same reaction tube. This is particularly advantageous when limited amounts of sample DNA are available for analysis. Conveniently, each of the sets of primers can be labeled with a different fluorochrome or one of a series of fluorochromes included in a reaction.

For microsatellite analysis, the size of the amplification product is proportional to the number of repeats (n) that are present at the locus specified by the primers. The size will be polymorphic in the population, and is therefore an allelic marker for that locus. For many applications, a panel of loci will be analyzed, usually at least about 5 loci, more usually at least about 10 loci. The combined information for the panel of loci serves as a "DNA fingerprint" for the individual.

The DNA fingerprint produced by the combination of microsatellite analysis and analysis of the canine amelogenin gene allows for identification of lost or stolen animals and confirmation of identity, such as may be required for show or stud dogs. Genotypes can be compared to assess the degree of relatedness between two individuals. Individuals that are closely related have a higher probability of shared alleles than unrelated individuals (see Chakraborty and Lin (1993) Hum. Biol. 65:875-895; and Hammond (1994) Am. J. Hum. Genet. 55:175-189). Knowledge of relatedness is useful for the improvement of breeding programs, and for increasing genetic diversity in a population. Canine DNA samples recovered from crime scenes may be used to provide forensic evidence.

The genotypes are useful for parentage testing. Individuals can be ruled out as possible sires or dams of an offspring in question by comparing their genotypes. Each individual must receive one allele from its mother and one from its father at each locus, so that putative parents that do not share an allele at every locus with the individual in question can be excluded from parentage. When using a set of microsatellite markers for parentage testing, it is important to know how powerful they are in terms of detection of false parentage. The formula for parentage exclusion (PE) states the probability that a given series of codominant alleles should detect a falsely recorded parent, Jamieson (1994) Anim. Genet. 25:37-44. The PE can be calculated for each locus, and for all of the loci combined.

In embodiments that include analyzing binding of at least one probe or primer to the canine amelogenin gene as well as binding of at least one probe or primer to a microsatellite locus, probes, primers and labels can be selected such that probes, primers, and labels can be used in a single multiplex analysis. For example, as illustrated in the Example herein, primers for the amelogenin gene were chosen that could be used in a 5 dye multiplex system for canine microsatellite markers. Therefore, primers were chosen that generated amplification products (i.e. markers) that did not overlap existing markers (120-156 bases) for a given label (See FIGS. 2-4).

Accordingly, minor changes were made to an initially discovered primer set (BFK90055 and BFK90052) in order to fit them into a canine microsatellite multiplex assay (FIGS. 1-4). BFK90065 which is 4 bases smaller than BFK90055, was used in place of BFK90055, and BFK90059 was used in place of BFK90052. BFK90059 is identical in sequence to BFK90052 but fluorescently labeled with NED instead of PET (Applied Biosystems). As reported herein, gender was tested using these primers in over 10,000 dog samples, and in all of these assays, gender was correctly identified. Examples of gender determination by the analysis of nucleic acid products derived from the use of canine amelogenin specific primers are illustrated in FIGS. 1-4.

Aspects of the present invention which include gender determination using the amelogenin gender markers disclosed herein, as well as genotyping using canine microsatellite markers, provide for the both a determination of gender and identity of a canine subject. This has the advantage of efficiently providing this information using an automated multiplexing system, of which many are known in the art.

Figure 2:
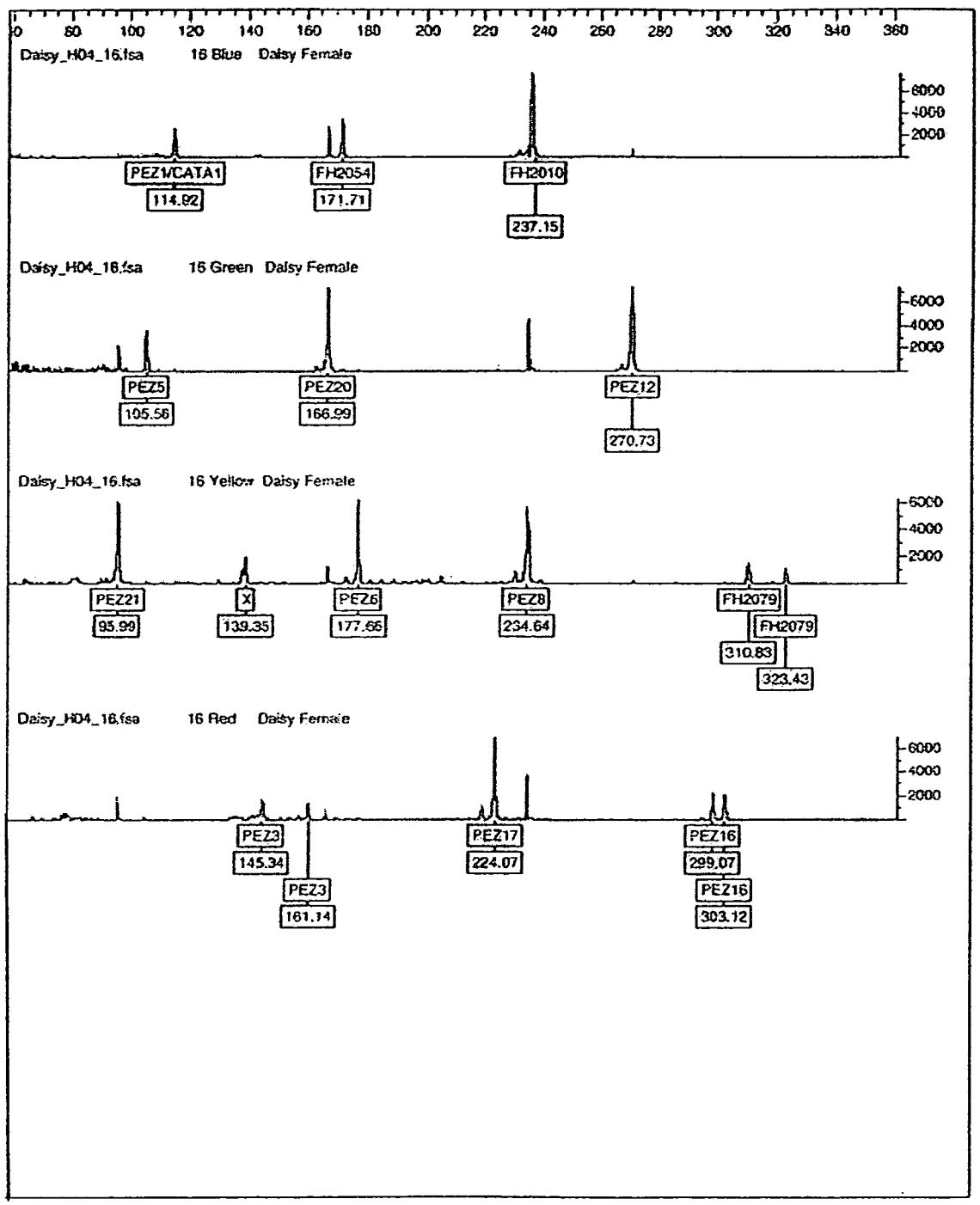
FIG. 2 illustrates multiplex PCR results for canine samples, wherein the multiplex PCR assay includes a gender marker and 13 microsatellite markers (i.e. STRs). The plots, generated using an ABI Prism, denote the various markers, including an X specific amplification product generated using BFK90059 and BFK90065. X and Y axis are as disclosed for FIG. 1. The plots were generated from a sample of a female canine subject using different colored labels, as indicated.
Figure 3:
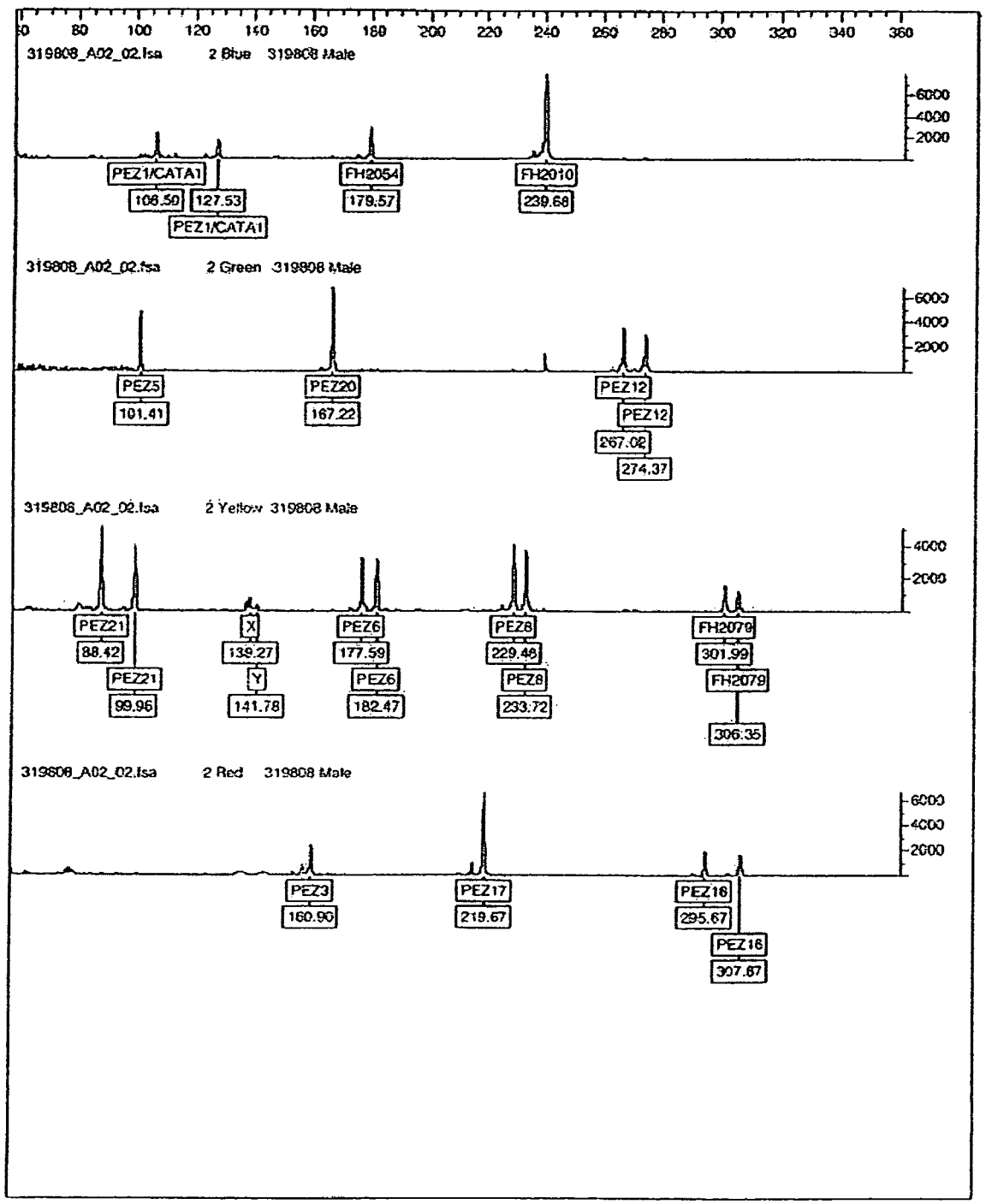
FIG. 3 illustrates multiplex PCR results for canine samples, wherein the multiplex PCR assay includes a gender marker and 13 microsatellite markers (i.e. STRs). The plots, generated using an ABI Prism, denote the various markers, including X and Y-specific amplification products (i.e. markers) generated using BFK90059 and BFK90065. X and Y axis are as disclosed for FIG. 1. The plots were generated from a male subject using different colored labels, as indicated.
Figure 4:
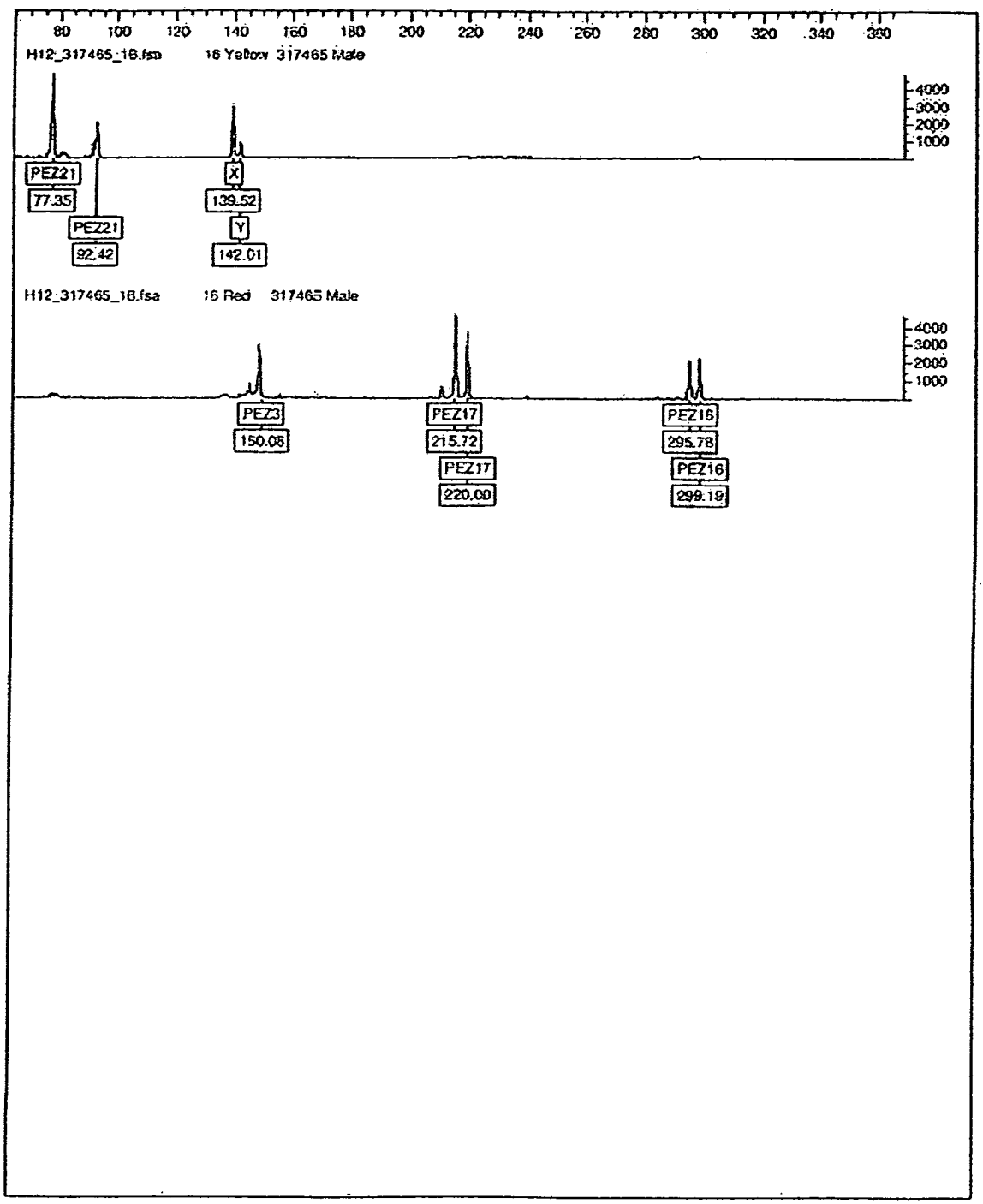
FIG. 4 illustrates multiplex PCR results for canine samples, wherein the multiplex PCR assay includes a gender marker and 4 microsatellite markers (i.e. STRs). The plots, generated using an ABI Prism, denote the various markers, including X and Y-specific amplification products (i.e. markers) generated using BFK90059 and BFK90065. X and Y axis are as disclosed for FIG. 1. The plots were generated from a sample from a male canine subject, using different colored labels, as indicated.

Accordingly, provided herein is a method for simultaneously determining gender, identity and parentage in a canine, that includes contacting a nucleic acid sample from a canine to be tested, with primers specific for canine amelogenin as disclosed herein, and probes and primers specific for DNA-based parentage and identity (e.g. microsatellite locus) in a multiplex reaction, and identifying the nucleic acid products, thereby determining gender, identity and parentage. This method is illustrated in the Example and FIGS. 2-4 provided herein. In other words, one embodiment the present invention provides a method and system, also referred to as a "comprehensive canine testing system," whereby the gender marker is included in a multiplex reaction that includes other markers, e.g., microsatellite markers, that provide the basis for identity and parentage testing. Therefore, the method can be multiplex genotyping reactions that utilize the gender markers disclosed herein, as well as short tandem repeats (STRs), also referred to as microsatellites. Microsatellite markers offer numerous benefits, including that these markers are evenly distributed across the genome, are highly polymorphic, and therefore, highly informative.

Microsatellite genotyping and gender data regarding a canine subject can be stored in a computer readable form, such as a database. Accordingly, in certain aspects of the invention, a dog owner provides a sample to a service provider for genotyping and gender analysis. For example, the sample can be sent by mailing the sample to the service provider. The service provider can then perform a gender determination and microsatellite genotyping, for example in a single multiplex reaction, as disclosed herein, and store the results in a database.

The database can be flat file databases, relational databases or object-oriented databases. The parts of the database can be internal databases, or external databases that are accessible to users. An internal database is a database maintained as a private database, typically maintained behind a firewall, by an enterprise. An external database is located outside an internal database, and is typically maintained by a different entity than an internal database.

Amelogenin gender markers are markers that are detectably different when generated from the X chromosome compared to the Y chromosome. For example, amelogenin gender markers include amplification products generated using primers disclosed herein that produce a different sized product when used to amplify a portion of the amelogenin gene on the X chromosome as compared to the product generated from the amelogenin gene on the Y chromosome. Amelogenin gender markers can also include restriction fragments that are detected using a probed of the present invention, that are a different size in the X chromosome amelogenin gene than the Y chromosome amelogenin gene. Microsatellite markers are markers that are detectably different depending on the number of repeats at a microsatellite locus.

In certain aspects, the microsatellite locus includes a repeated tetranucleotide motif consisting of AAA or TTT, with the fourth residue of the tetranucleotide repeat motif being any one of G, C, A or T. In another aspect, the microsatellite locus comprises a repeated motif selected from AAAG, GAAA, AAAT, TTTC, CTTT, TTTA, AAGG, GAAT, GAAG, GAAAA, AAAAAG, TGC and TTC.

In certain aspects the microsatellite locus is at least one of PEZ1/CATA1, PEZ3, PEZ5, PEZ6, PEZ8, PEZ10, PEZ11, PEZ12, PEZ13, PEZ15, PEZ16, PEZ17, PEZ20, PEZ21, FH2010 ("FH" denotes a Fred Hutchinson marker), FH2054, and FH2079 (See Tables 4-6). Accordingly, for example, binding of at least one primer or probe to each of PEZ1/CATA1, PEZ3, PEZ5, PEZ6, PEZ8, PEZ12, PEZ20, FH2010 (Fred Hutchinson markers), FH2054, and FH2079, or any combination thereof, is detected. For example, a panel of 1, 2, 3, 4, 5, 6, 7, 8, 9, 10, 11, 12, 13, 14, 15, 16, or 17 of the microsatellites can be genotyped. In certain aspects, this method is a multiplex amplification reaction that employs a primer pair for generating a different sized amplification product for the X chromosome amelogenin gene from that obtained for the Y chromosome amelogenin gene, as disclosed herein, as well as the primer pairs listed in Tables 4 through 6 for each of PEZ1/CATA1, PEZ3, PEZ5, PEZ6, PEZ8, PEZ12, PEZ20, FH2010, FH2054, and FH2079. Thus, this embodiment is a 10-plex satellite marker panel along with an amelogenin gender marker.

In another example, binding of at least one primer or probe to each of PEZ10, PEZ11, PEZ13, PEZ15, PEZ16, PEZ17, and PEZ21, or any combination thereof, is detected. For example, this method can be a multiplex amplification reaction that employs a primer pair for generating a different sized amplification product for the X chromosome amelogenin gene from that obtained for the Y chromosome amelogenin gene, as disclosed herein, as well as the primer pairs listed in Tables 4 through 6 for each of PEZ10, PEZ11, PEZ13, PEZ15, PEZ16, PEZ17, and PEZ21. Thus, this embodiment is a 7-plex satellite marker panel along with an amelogenin gender marker.

In yet another example, binding is detected for at least one primer or probe to each of PEZ1/CATA1, PEZ3, PEZ5, PEZ6, PEZ8, PEZ12, PEZ16, PEZ17, PEZ20, PEZ21, FH2010, FH2054, and FH2079, or any combination thereof. For example, this method can be a multiplex amplification reaction that employs a primer pair for generating a different size amplification product for the X chromosome amelogenin gene from that obtained for the Y chromosome amelogenin gene, as disclosed herein, as well as the primer pairs listed in Tables 4 through 6 for each of PEZ1/CATA1, PEZ3, PEZ5, PEZ6, PEZ8, PEZ12, PEZ16, PEZ17, PEZ20, PEZ21, FH2010, FH2054, and FH2079. Thus, this embodiment is a 13-plex satellite marker panel along with an amelogenin gender marker.

In another embodiment, the present invention provides a kit for performing the methods provided herein. Such a kit can include, for example, at least one set of primers useful for amplifying canine amelogenin and optionally at least one other pair of primers useful for amplifying microsatellite DNA repeats. In certain aspects the kit includes a pair of primers useful for amplifying canine amelogenin and a panel of primers useful for amplifying a panel of microsatellite DNA repeats. The primers can be conjugated to a detectable marker, and can be conjugated to different labels to facilitate multiplex amplification. In a preferred embodiment, the primers include SEQ ID NOS: 3 or 4 and SEQ ID NO:5.

The present invention discloses the nucleotide and polypeptide sequence of a portion of the canine amelogenin gene, which as indicated above, can be used to identify the nucleotide sequence of the entire canine. (e.g. dog) amelogenin X chromosome gene and Y chromosome gene, as well as the polypeptide sequence of canine amelogenin from the X chromosome and the Y chromosome. Accordingly, in another embodiment, the present invention provides an isolated polynucleotide that includes all or a portion of a canine (e.g. dog) amelogenin gene, for example at least 25, 50, 75, 100, 150, 200, 250, 300, 400, 500, 750, or 1000 contiguous nucleotides of a canine amelogenin gene, or a complement thereof, or a polynucleotide at least 75, 80, 85, 90, 95, 96, 97, 98, 99, or 99.9% identical thereto. In one aspect, the present invention provides an isolated polynucleotide that includes at least 25, 50, 75, 100, 150, 200, 250, 300, 400, or 492 contiguous nucleotides of SEQ ID NOS:22 or 23, or a complement thereof, or an isolated polynucleotide that is 85, 90, 95, 96, 97, 98, 99, or 99.9% identical to these sequences; or an isolated polynucleotide that includes at least 400, 450, 500, 550, 600, 650, or 680 contiguous nucleotides of SEQ ID NO:23, or a complement thereof, or an isolated polynucleotide that is 85, 90, 95, 96, 97, 98, 99, or 99.9% identical to these sequences. In certain aspects, the present invention provides an isolated polypeptide that includes SEQ ID NO:22 or SEQ ID NO:23. SEQ ID NOS:22 and 23 provide the nucleotide sequence of a portion of the canine amelogenin gene on the X and Y chromosomes, respectively. It will be understood that based on the present disclosure, routine methods can be used to identify the entire canine amelogenin gene.

The amelogenin gene is involved in the production of tooth enamel. Therefore, in addition to uses of the amelogenin gene and polypeptide (see below) sequences in gender determination, these compositions are also useful for identifying new methods to diagnose and treat canine tooth disorders. Furthermore, these compositions can be used for improved tooth enamel formation.

In another embodiment, the present invention provides a vector comprising the isolated polynucleotide portion of the canine amelogenin gene disclosed above. The term "vector" refers to a plasmid, virus or other vehicle known in the art that has been manipulated by insertion or incorporation of a nucleic acid sequence.

Methods that are well known in the art can be used to construct vectors of the present invention, including in vitro recombinant DNA techniques, synthetic techniques, and in vivo recombination/genetic techniques (See, for example, the techniques described in Maniatis et al. 1989 Molecular Cloning A Laboratory Manual, Cold Spring Harbor Laboratory, N.Y., incorporated herein in its entirety by reference).

In another aspect, the present invention provides an isolated cell that includes a vector of the present invention. The cell can be prokaryotic or eukaryotic. Techniques for incorporated vectors into prokaryotic and eukaryotic cells are well known in the art. In certain aspects, the cells are canine cells. In other aspects, the cells are bacterial cells. In still other aspects, the cells are human cells.

In another embodiment, the present invention provides an isolated polypeptide encoded by SEQ ID NO:22 or SEQ ID NO:23. Furthermore, in certain embodiment, the present invention provides an antibody that specifically binds to the isolated polypeptides of the present invention.

In another embodiment, the present invention provide an isolated polynucleotide that encodes the polypeptide encoded by SEQ ID NOS:22 or 23, or a complement thereof.

The following example is intended to illustrate but not limit the invention.

EXAMPLE 1

Determination of Canine Gender

Canine Amelogenin Primer Design

All canine DNA samples analyzed in this example, were dog DNA samples. Several sets of primers were designed based on similarities among canine, human and other mammalian sequences corresponding to several sites along the amelogenin genes. One set of primers, BFK90004 (SEQ ID NO:2) and BFK90006 (SEQ ID NO: 1), when used to PCR amplify male or female canine DNA, produced many bands on an agarose gel although the expected size (somewhat larger than 2000 base pairs, based on human sequence) was very faint from female canine DNA and strong from male canine DNA. Primers BFK90004 (SEQ ID NO:2) and BFK90006 (SEQ ID NO:1) correspond to sequences in the human amelogenin exons 3 and 2 and span intron 2 which is about 1940 bp on the X chromosome and 2500 bp on the Y chromosome. BFK90006 (SEQ ID NO:1), which includes the ATG start codon for the gene, with one degenerate base, is identical within human, equine, bovine and goat X and Y chromosomes and with other mammals where amelogenin chromosomal locations are either unknown or only X-linked, such as porcine and mouse. BFK90004 (SEQ ID NO:2) is the reverse complement of one of the primers of a set that was used to amplify canine fragments successfully and is identical in human X and Y chromosomes.

Amplification and Cloning of Canine Amelogenin DNA

DNA was isolated from various male and female dogs using either the PUREGENE DNA Isolation Kit for blood (Gentra Systems) or a chelex prep for buccal swabs (Walsh et al. 1991). PCR was performed on 300 ng of male or female canine genomic DNA using 10 pmol each of primers BFK90004 (SEQ ID NO:2) and BFK90006 (SEQ ID NO:1), 1× Taq Gold Buffer (Applied Biosystems), 2 mM $MgCl_2$, 0.2 mM each dNTP (Applied Biosystems) and 2 units of AmpliTaq Gold Polymerase (Applied Biosystems) in a 50 µl reaction. The following PCR conditions were used in a Applied Biosystems 9700 thermocycler: 95° C. for 10 minutes followed by 35 cycles of 30 seconds at 94° C., 30 seconds at either 56° C. or 58° C., and 1 minute 30 seconds at 72° C. followed by a final extension of 72° C. for 20 minutes. 25 µl of each product was fractionated alongside a low mass DNA ladder (BRL (now Life Technologies)) on a 0.85% SeaPlaque GTG (BioWhittaker) agarose gel in TAE buffer containing GelStar (BioWhittaker) stain. Bands of three different sizes (>2 kb, >1.2 kb and <1.2 kb) were excised from the gel, purified with a QIAquick Gel Extraction Kit (Qiagen) and eluted in 30 µl. 2 µl of each DNA fragment was ligated into a pCR'4-TOPO vector using the TOPO TA Cloning Kit for Sequencing (Invitrogen), electroporated into TOP 10 cells (Invitrogen) and plated on agar plates containing 50 µg/ml kanamycin. For each construct, 16 resulting bacterial colonies were individually picked by touching with a sterile toothpick and lightly swabbing into the bottom of a 200 µl PCR tube. The inserts were amplified in a 20 µl reaction containing 5 pmol each of M13 forward and reverse primers, 1× Taq Gold Buffer, 2 mM $MgCl_2$, 0.2 mM each dNTP and 1 units of AmpliTaq Gold Polymerase in an Applied Biosystems 9700 thermocycler using the conditions above for 30 cycles instead of 35 and with a 56° C. annealing temperature. To test for inserts and sizes, 5 µl of the reactions were fractionated on a 0.8% agarose gel.

Sequencing

For clones containing inserts, 2.5 µl of the PCR product was removed to a tube containing 2 µl of a solution containing 1 unit each of Exonuclease I and Shrimp Alkaline Phosphatase (USB) per microliter in water and incubated at 37° C. for one hour followed by inactivation at 75° C. for 20 minutes. Sequencing was carried out with a BigDye Terminator V3.0 Cycle Sequencing Kit (Applied Biosystems) using 2 μl of the treated fragments and 3.2 pmol of either T3 or T7 primer from the TA cloning kit (Invitrogen). Reactions were ethanol precipitated, resuspended in 20 μl of Hi-Di Formamide, denatured and run on an ABI Prism 3100 using POP6 and a 50 inch capillary array. Resulting sequences were analyzed and compared using Lasergene software (DNASTAR).

The constructs of the expected size (>2 kb) produced sequences consistent with an amelogenin coding region. Based on differences within our canine sequences, new primers were developed.

Gender Marker Primer Design and Fragment Detection

Sequences that were identical between the putative X and Y canine genes and that spanned insertion/deletion areas were chosen for primer design with the aim of producing fragments of different sizes for each chromosome. One region of the canine amelogenin gene that was identified as useful in gender determination is shown in Tables 1 and 3.

Primers were chosen such that they could be used in a 5 dye multiplex system for canine microsatellite markers. Therefore, primers were chosen that generated amplification products (i.e. markers) without overlapping existing markers (120-156 bases). Furthermore, primer sets were chosen would not amplify human DNA, which would be a potential source of contamination. One primer of each set was fluorescently labeled. Exemplary primers that were identified are shown in Table 2.

Male or female canine DNA (10 ng) was each amplified in an 8 μl reaction using 0.5 pmoles of each primer, 1.4× Taq Gold Buffer, 3 mM MgCl$_2$, 0.27 mM each dNTP and 0.18 units of AmpliTaq Gold Polymerase in a Perkin Elmer 9600 thermocycler. PCR conditions were: 95° C. for 12 minutes followed by 35 cycles of 30 seconds at 94° C., 30 seconds at 58° C., and 1 minute at 72° C. followed by a final extension of 72° C. for 30 minutes. Following PCR the samples were diluted 30 fold and 2 μl were added to 10 μl Hi-Di Formamide containing 0.1 μl GeneScan-500 LIZ Size Standard (Applied Biosystems), denatured and run on an ABI Prism 3100 using POP4 and a 36 inch capillary array and analysed using Genotyper software (Applied Biosystems). One set of primers (BFK90052 and BFK90055) produced a 143 base band in male and female canine samples and an extra band of 146 bases in the male sample. These results were consistent across 3 male and 3 female dog samples.

Minor changes were made in the primer set in order to fit them into a canine microsatellite multiplex assay (FIGS. 2-4). BFK90065 which is 4 bases smaller than BFK90055, was used in place of BFK90055, and BFK90059 was used in place of BFK90052. BFK90059 is identical in sequence to BFK90052 but fluorescently labeled with NED instead of PET (Applied Biosystems). Examples of gender determinations using these primers are provided in FIG. 1. Two amplification products (denoted "X" and "Y" in FIGS. 1-4), were generated using male canine subjects. Amplification products generated from female subjects, on the other hand, included only one product (denoted "X" in FIGS. 1-4). Gender has been tested using these primers in over 10,000 dog samples from a wide range of breeds, and in these assays, gender was correctly identified.

Assay of Multiplexed PCR Primers for Detection of Polymorphism:

PCR was performed on canine genomic DNA using microsatellite markers pooled with the gender marker using the GeneAmp™ PCR process in a 9600 thermocycler (Perkin Elmer, Norwalk Conn.). Post-PCR products were run on an ABI PRISM 3100 Genetic Analyzer (Applied Biosystems, Foster City Calif.). GS500LIZ (Applied Biosystems, Foster City Calif.) markers were present in each sample as internal size standards. PCR products were sized and genotyped using GeneScan™ Analysis Software and Genotyper™ Software (Applied Biosystems, Foster City Calif.). Primers for microsatellite genotyping are listed in Tables 4 through 6. More specific PCR conditions are listed below. Examples of genotyping results are illustrated in FIGS. 2 through 4. Allele products are labeled with the marker name and size in base pairs. Alleles for the gender marker are labeled as X or Y with base pair sizing. FIG. 2 is from a female dog and FIGS. 3 and 4 are from male dogs. The results illustrated in FIGS. 2-4 establish that methods of the present invention can provide both genotype and gender information in a single reaction.

Specific Example of a Method of the Invention

A specific set of reaction and PCR conditions that can be used for gender marker identification using methods for determining gender disclosed herein, within a multiplex genotyping reaction disclosed above, are as follows: 0.29 pmoles of each of BFK90059 and BFK90065 primers, 1.5× Taq Gold Buffer, 2.5 mM MgCl$_2$, 0.175 mM each dNTP and 0.75 units of AmpliTaq Gold Polymerase in an 5 μl reaction containing a highly variable amount of canine DNA (approximately 0.5-100 ng). PCR: 95° C. for 12 minutes, 15 cycles of 30 seconds at 94° C., 30 seconds at 64° C. decreasing 0.2° C./cycle to 61° C., and 1 minute at 72° C., followed by 20 cycles of 30 seconds at 94° C., 30 seconds at 61° C., and 1 minute at 72° C., followed by a final extension of 72° C. for 45 minutes in a Perkin Elmer 9600 thermocycler.

Sequence Support

The sequence data provides evidence that the disclosed primers are specific for the canine amelogenin gene. Table 7 provides an alignment of sequence information obtained from canine compared to human amelogenin sequences. When human DNA was tested using primers BFK90065 and BFK90059, a faint 143 base band was detected in female and male but no 146 base band was detected in any human sample thus eliminating any concern of human DNA contamination. These results were expected since BFK90065 is in a highly conserved region near the initial amelogenin ATG start codon whereas BFK90059 lies within an intron and has 19/22 bases identical to human amelogenin-X but only 15/22 bases identical to human amelogenin-Y with the 3' end of the primer being most different (Table 1).

TABLE 1

Comparison of Canine gender marker sequence with Human amelogenin sequence (italics denote primer binding region and bold denotes differences from consensus) (contiguous human sequences from table below are found in SEQ ID NO:20 (X chromosome) and SEQ ID NO:21 (Y chromosome) and contiguous canine sequences are found in SEQ ID NO:10 (X chromosome) and SEQ ID NO:11 (Y chromosome).

| | SEQ ID NO: | |
|---|---|---|
| Human X | 12 | *GATTTTATTTGCCTGCCT*CCTGGGAGCAGCTTTTTGCCATGCCTGTGAGTAAAACACCCCTTTCATAAGTCAGTGTC |
| Human Y | 13 | *GATTTTGTTTGCCTGCCT*TGTGGGAGCAGCTTTTGCCATGCCTGTGAGTAAAACATTCTTTGCATAAGTTG-TGTC |
| Canine X | 14 | *GATTTTGTTTGCCTGCCT*CCTGGGAGCAGCCTTTGCTATGCCCGTGAGTAAAATACCCCTG-CATAA-T-A-T-T- |
| Canine Y | 15 | *GATTTTGTTTGCCTGCCT*CCTGGGAGCAGCCTTTCAGTATGCCTGTGAGTAAAAT-----TT-CC-AA-T-T-T-C- |
| | | BFK90065 → |
| Human X | 16 | CAATTTCACAAACTTGGACATAAAAATCTGC-TCATA------GTT-GG-TGAAA-TT-AGGGTTTAAAAACAGTATGA*GATC* |
| Human Y | 17 | CAATTT-ACAAATGGAAATAAGAATTTG-TC---CCCC-AGCT-GG-GAAACTTTCC-AAGGTTTAAAACAGTTTGAGCTA |
| Canine X | 18 | CAATTTCACAAGCTTGGAAATAAAAGTCTGCC-CC-AC----AGTT-GG-T-AAA-CTTTAGGGTTTAAGACAGTACAAGATC |
| Canine Y | 19 | CAATTTCACAAGCTTGGAAATAAAAATCTGCCTCAGATTTTTATTTAGGGTTAAA-TTTAAGGGTTTAAGACAGTACAAGATC |
| | | ← BFK90059 |

TABLE 2

Canine amelogenin gender marker primers and sequence data

| Primer Sequence | Comments | SEQ ID NO: |
|---|---|---|
| BFK90006 5' *ATGGGGACCTGGATTTRTTTG* 3' | (R = A or G) | 1 |
| BFK90004 5' CCAGGGTGCCCAGGATGAGGT 3' | | 2 |
| BFK90055 5' GATTTTGTTTGCCTGCCTCCTG 3' | | 3 |
| BFK90065 5' GATTTTGTTTGCCTGCCT 3' | (BF0055 - 4 bases) | 4 |
| BFK90052 5' GATCTTGTACTGTCTTAAACCC 3' | (DYE-LABELED A) | 5 |
| BFK90059 5' GATCTTGTACTGTCTTAAACCC 3' | (DYE-LABELED B) | 5 |

TABLE 3

Canine Gender Marker Sequences (italics denotes primer binding region and bold denotes differences in sequence)

| | SEQ ID NO: | |
|---|---|---|
| Canine X (1-76) | 6 | *GATTTTGTTTGCCTGCCT*CCTGGGAGCAGCCTTTGCTATGCCCGTGAGTAAAATACCCCTGCATAATATTCAATTT |
| Canine Y (1-70) | 7 | *GATTTTGTTTGCCTGCCT*CCTGGGAGCAGCCTTCAGTATGCCTGTGAGTAAAAT-----TTCC-AATTTCCAATTT |
| | | BFK90065 → |
| Canine X (77-143) | 8 | CACAAGCTTGGAAATAAAAGTCTGCC-CC-ACC----AGTT-GG-T-AACTTT*AGGGTTTAAGACAGTACAAGATC* |
| Canine Y (71-146) | 9 | CACAAGCTTGGAAATAAAAATCTGCCTCAGATTTTTATTTAGGGTTAAATTTAA*GGGTTTAAGACAGTACAAGATC* |
| | | ← BFK90059 |

TABLE 4

Microsatellite primers and sequences

| Primer 1 SEQ ID NO: | Primer 2 SEQ ID NO | Locus ID SEQ ID NO | PEZ Nomenclature | Primer 1 SEQ ID NO: | Primer 2 SEQ ID NO | Locus ID SEQ ID NO | PEZ Nomenclature |
|---|---|---|---|---|---|---|---|
| 52 | 72 | 32 | PEZ3 | 56 | 76 | 36 | PEZ9 |
| 53 | 73 | 33 | PEZ6 | 57 | 77 | 37 | PEZ5 |
| 54 | 74 | 34 | PEZ7 | 58 | 78 | 38 | PEZ10 |
| 55 | 75 | 35 | PEZ8 | 59 | 79 | 39 | PEZ11 |

TABLE 4-continued

Microsatellite primers and sequences

| Primer 1 SEQ ID NO: | Primer 2 SEQ ID NO | Locus ID SEQ ID NO | PEZ Nomenclature |
|---|---|---|---|
| 60 | 80 | 40 | PEZ13 |
| 61 | 81 | 41 | PEZ20 |
| 62 | 82 | 42 | PEZ14 |
| 63 | 83 | 43 | PEZ21 |
| 64 | 84 | 44 | PEZ15 |
| 65 | 85 | 45 | PEZ16 |
| 66 | 86 | 46 | PEZ19 |
| 67 | 87 | 47 | PEZ22 |
| 68 | 88 | 48 | PEZ12 |
| 69 | 89 | 49 | PEZ18 |
| 70 | 90 | 50 | PEZ17 |
| 71 | 91 | 51 | PEZ2 |

TABLE 5

FHC Microsatellite Markers (all are tetra repeat motifs)

| Locus | Size range | Chromos. Location | Forward | SEQ ID NO: | Reverse | SEQ ID NO: |
|---|---|---|---|---|---|---|
| FH2054 | 135-179 | CFA12 | GCCTTATTCATTGCAGTTAGGG | 92 | ATGCTGAGTTTTGAACTTTCCC | 95 |
| FH2079 | 263-299 | CFA24 | CAGCCGAGCACATGGTTT | 93 | ATTGATTCTGATATGCCCAGC | 96 |
| FH2010 | 220-248 | CFA24 | AAATGGAACAGTTGAGCATGC | 94 | CCCCTTACAGCTTCATTTTCC | 97 |

TABLE 6

Microsatellite Marker PEZ1/CATA1 (tetra repeat motif)

| Locus | Size range | Chromos. Location | Forward | SEQ ID NO: | Reverse | SEQ ID NO: |
|---|---|---|---|---|---|---|
| PEZ1/CATA1 | 95-133 | CFA07 | GGCTGTCACTTTTCCCTTTC | 98 | CACCACAATCTCTCTCATAAATAC | 99 |

TABLE 7

Comparison of Human and Canine X and Y amelogenin sequences and below them, the predicted proteins.
Bolded amino acids indicate difference from consensus.
The italicized sequences indicates the beginning of an intron known in human and assumed in canine.

| | SEQ ID NO: | |
|---|---|---|
| Human X | 24 | ATGGGGACCTGGATTTTATTTGCCTGCCTCCTGGGAGCAGCTTTTGCCATGCCT*GTGAGTAAAA* |
| | 25 | M G T W I L F A C L L G A A F A M P |
| Human Y | 26 | ATGGGGACCTGGATTTTGTTTGCCTGCCTTGTGGGAGCAGCTTTTGCCATGCCT*GTGAGTAAAA* |
| | 27 | M G T W I L F A C L V G A A F A M P |
| Canine X | 28 | ATGGGGACCTGGATTTTGTTTGCCTGCCTCCTGGGAGCAGCCTTTGCTATGCCC*GTGAGTAAAA* |
| | 29 | M G T W I L F A C L L G A A F A M P |
| Canine Y | 30 | ATGGGGACCTGGATTTTGTTTGCCTGCCTCCTGGGAGCAGCCTTCAGTATGCCT*GTGAGTAAAA* |
| | 31 | M G T W I L F A C L L G A A F S M P |

REFERENCES

Buel E, Wang G, Schwartz M. (1995) PCR Amplification of Animal DNA with Human X-Y Amelogenin Primers Used in Gender Determination. J Forensic Sci 40:641-644.

Chen C M, Hu C L, Wang C H, Hung C M, Wu H K, Choo K B, Cheng W T. (1999) Gender determination in single bovine blastomeres by Polymerase chain reaction amplification of sex-specific polymorphic fragments in the amelogenin gene. Mol Reprod Dev 54(3):209-214.

Hasegawa T, Sato F, Ishida N, Fukushima Y, Mukoyama H. (2000) Sex Determinaton by Simultaneous Amplification of Equine SRY and Amelogenin Genes. J Vet Med Sci 62(10):1109-1110.

Sullivan K M, Mannucci A, Kimpton C P, Gill P. (1993) A rapid and quantitative DNA sex test: fluorescence-based PCR analysis of X-Y homologous gene amelogenin Biotechniques 15:636-641.

Walsh P S, Metzger D A, Higuchi R. (1991) Chelex 100 as a medium for simple extraction of DNA for PRC-based typing from forensic material. Biotechniques 10:506-518.

Griffiths, R., Daan, S., Dijkstra, C. (1996) Sex identification in birds using two CHD genes. Proc. R. Soc. Lond. B Biol. Sci. 263(1374):1251-6.

Although the invention has been described with reference to the above example, it will be understood that modifications and variations are encompassed within the spirit and scope of the invention. Accordingly, the invention is limited only by the following claims.

What is claimed is:

1. A method for determining the gender of a subject from the canis familiaris species, comprising:
   a) contacting a nucleic acid sample from the subject with a first and a second oligonucleotide primer, wherein the first and/or second oligonucleotide primer is complementary to consensus regions between SEQ ID NO:22 and SEQ ID NO:23, and wherein such first and second primers flank non-consensus regions between SEQ ID NO:22 and SEQ ID NO:23;
   b) amplifying the flanked non-consensus regions, wherein the flanked non-consensus regions of SEQ ID NO:22 contain at least one gap in sequence alignment compared to the flanked non-consensus regions of SEQ ID NO:23, such that different length amplification products result if sequences comprising both SEQ ID NO:22 and SEQ ID NO:23 are present in the sample; and
   c) detecting amplification products resulting from step (b),
wherein detection of amplification products of different lengths correlates with male gender.

2. The method of claim 1, comprising determining the presence of amplified products of SEQ ID NO: 10 and SEQ ID NO:11.

3. The method of claim 2, wherein the first oligonucleotide primer binds to SEQ ID NO:6 and SEQ ID NO:7 and the second oligonucleotide primer binds to SEQ ID NO:8 and SEQ ID NO:9.

4. The method of claim 3, wherein the first primer comprises at least 10 nucleotides of SEQ ID NO:3 and the second primer comprises at least 10 nucleotides of SEQ ID NO:5.

5. The method of claim 4, wherein the first primer is SEQ ID NO:3 and the second primer is SEQ ID NO:5.

6. The method of claim 4, wherein the first primer is SEQ ID NO:4 and the second primer is SEQ ID NO:5.

7. The method of claim 4, wherein a first length is indicative of the non-consensus region of SEQ ID NO:22 and a second length is indicative of the non-consensus region of SEQ ID NO:23.

8. A method for determining the gender of a subject from the canis familiaris species, comprising:
   a) contacting a nucleic acid sample from the subject with a first and a second oligonucleotide primer, wherein the first and second oligonucleotide primers comprise sequences which are complementary to consensus regions between SEQ ID NO:22 and SEQ ID NO:23, and wherein such first and second primers flank non-consensus regions between SEQ ID NO:22 and SEQ ID NO:23;

b) amplifying the non-consensus regions, wherein the non-consensus regions of SEQ ID NO:22 contain at least one gap in sequence alignment compared to the non-consensus regions of SEQ ID NO:23, such that a single product results if non-consensus sequences of SEQ ID NO:23 are absent in the sample; and c) determining the presence or absence of the non-consensus regions in products resulting from the amplification in step (b), wherein failure to determine the non-consensus regions comprising SEQ ID NO: 23 correlates with female gender.

9. The method of claim 8, wherein a first oligonucleotide primer binds to SEQ ID NO:6 and/or SEQ ID NO:7 and a second oligonucleotide primer binds to SEQ ID NO:8 and/or SEQ ID NO:9.

10. The method of claim 1 or 8 further comprising:

i) contacting a portion of the nucleic acid sample of step a) with a second set of primers which are complementary to at least one microsatellite locus;

ii) amplifying the microsatellite locus; and iii) detecting different amplified products.

11. The method of claim 10, wherein the microsatellite locus is at least one of PEZ1/CATA1, PEZ3, PEZ5, PEZ6, PEZ8, PEZ10, PEZ11, PEZ12, PEZ13, PEZ15, PEZ16, PEZ17, PEZ20, PEZ21, FH2010, FH2054, and FH2079.

* * * * *

SEQUENCE LISTING

```
<160> NUMBER OF SEQ ID NOS: 99

<210> SEQ ID NO 1
<211> LENGTH: 21
<212> TYPE: DNA
<213> ORGANISM: Artificial sequence
<220> FEATURE:
<223> OTHER INFORMATION: Primer

<400> SEQUENCE: 1
atggggacct ggatttrttt g                                              21

<210> SEQ ID NO 2
<211> LENGTH: 21
<212> TYPE: DNA
<213> ORGANISM: Artificial sequence
<220> FEATURE:
<223> OTHER INFORMATION: Primer

<400> SEQUENCE: 2
ccagggtgcc caggatgagg t                                              21

<210> SEQ ID NO 3
<211> LENGTH: 22
<212> TYPE: DNA
<213> ORGANISM: Artificial sequence
<220> FEATURE:
<223> OTHER INFORMATION: Primer

<400> SEQUENCE: 3
gattttgttt gcctgcctcc tg                                             22

<210> SEQ ID NO 4
<211> LENGTH: 18
<212> TYPE: DNA
<213> ORGANISM: Artificial sequence
<220> FEATURE:
<223> OTHER INFORMATION: Primer

<400> SEQUENCE: 4
gattttgttt gcctgcct                                                  18

<210> SEQ ID NO 5
<211> LENGTH: 22
<212> TYPE: DNA
<213> ORGANISM: Artificial sequence
<220> FEATURE:
<223> OTHER INFORMATION: Primer

<400> SEQUENCE: 5
gatcttgtac tgtcttaaac cc                                             22
```

<210> SEQ ID NO 6
<211> LENGTH: 76
<212> TYPE: DNA
<213> ORGANISM: Canis familiaris X

<400> SEQUENCE: 6

```
gattttgttt gcctgcctcc tgggagcagc ctttgctatg cccgtgagta aataccccct    60
gcataatatt caattt                                                    76
```

<210> SEQ ID NO 7
<211> LENGTH: 70
<212> TYPE: DNA
<213> ORGANISM: Canis familiaris Y

<400> SEQUENCE: 7

```
gattttgttt gcctgcctcc tgggagcagc cttcagtatg cctgtgagta aatttccaa     60 tttccaattt                                                           70
```

<210> SEQ ID NO 8
<211> LENGTH: 67
<212> TYPE: DNA
<213> ORGANISM: Canis familiaris X

<400> SEQUENCE: 8

```
cacaagcttg gaaataaaag tctgccccac cagttggtaa ctttagggtt taagacagta    60
caagatc                                                              67
```

<210> SEQ ID NO 9
<211> LENGTH: 76
<212> TYPE: DNA
<213> ORGANISM: Canis familiaris Y

<400> SEQUENCE: 9

```
cacaagcttg gaaataaaaa tctgcctcag attttattt agggttaaat ttaagggttt     60
aagacagtac aagatc                                                    76
```

<210> SEQ ID NO 10
<211> LENGTH: 143
<212> TYPE: DNA
<213> ORGANISM: Canis familiaris X

<400> SEQUENCE: 10

```
gattttgttt gcctgcctcc tgggagcagc ctttgctatg cccgtgagta aataccccct    60
gcataatatt caatttcaca agcttggaaa taaaagtctg ccccaccagt tggtaacttt   120
agggtttaag acagtacaag atc                                           143
```

<210> SEQ ID NO 11
<211> LENGTH: 146
<212> TYPE: DNA
<213> ORGANISM: Canis familiaris Y

<400> SEQUENCE: 11

```
gattttgttt gcctgcctcc tgggagcagc cttcagtatg cctgtgagta aatttccaa     60 tttccaattt cacaagcttg gaaataaaaa tctgcctcag attttattt agggttaaat   120 ttaagggttt aagacagtac aagatc                                        146
```

<210> SEQ ID NO 12
<211> LENGTH: 77
<212> TYPE: DNA
<213> ORGANISM: Homo sapiens  X

<400> SEQUENCE: 12
gattttattt gcctgcctcc tgggagcagc tttttgccat gcctgtgagt aaaacacccc      60
tttcataagt cagtgtc                                                    77

<210> SEQ ID NO 13
<211> LENGTH: 75
<212> TYPE: DNA
<213> ORGANISM: Homo sapiens  Y

<400> SEQUENCE: 13
gattttgttt gcctgccttg tgggagcagc ttttgccatg cctgtgagta aacattctt      60 tgcataagtt gtgtc                                                      75

<210> SEQ ID NO 14
<211> LENGTH: 70
<212> TYPE: DNA
<213> ORGANISM: Canis familiaris  X

<400> SEQUENCE: 14
gattttgttt gcctgcctcc tgggagcagc ctttgctatg cccgtgagta aataccccct      60
gcataatatt                                                            70

<210> SEQ ID NO 15
<211> LENGTH: 65
<212> TYPE: DNA
<213> ORGANISM: Canis familiaris  Y

<400> SEQUENCE: 15
gattttgttt gcctgcctcc tgggagcagc ctttcagtat gcctgtgagt aaaatttcca      60
atttc                                                                 65

<210> SEQ ID NO 16
<211> LENGTH: 71
<212> TYPE: DNA
<213> ORGANISM: Homo sapiens  X

<400> SEQUENCE: 16
caatttcaca aacttggaca taaaaatctg ctcatagttg gtgaaattag ggtttaaaac      60
agtatgagat c                                                          71

<210> SEQ ID NO 17
<211> LENGTH: 72
<212> TYPE: DNA
<213> ORGANISM: Homo sapiens  Y

<400> SEQUENCE: 17
caatttacaa atggaaataa gaatttgtcc cccagctggg aaactttcca aggtttaaaa      60
cagtttgagc ta                                                         72

<210> SEQ ID NO 18
<211> LENGTH: 73
<212> TYPE: DNA
<213> ORGANISM: Canis familiaris  X

<400> SEQUENCE: 18

```
caatttcaca agcttggaaa taaaagtctg ccccacagtt ggtaaacttt agggtttaag    60
acagtacaag atc                                                      73

<210> SEQ ID NO 19
<211> LENGTH: 82
<212> TYPE: DNA
<213> ORGANISM: Canis familiaris  Y

<400> SEQUENCE: 19
caatttcaca agcttggaaa taaaaatctg cctcagattt ttatttaggg ttaaatttaa    60
gggtttaaga cagtacaaga tc                                            82

<210> SEQ ID NO 20
<211> LENGTH: 148
<212> TYPE: DNA
<213> ORGANISM: Homo sapiens  X

<400> SEQUENCE: 20
gattttattt gcctgcctcc tgggagcagc tttttgccat gcctgtgagt aaaacacccc    60
tttcataagt cagtgtccaa tttcacaaac ttggacataa aaatctgctc atagttggtg   120
aaattagggt ttaaaacagt atgagatc                                     148

<210> SEQ ID NO 21
<211> LENGTH: 142
<212> TYPE: DNA
<213> ORGANISM: Homo sapiens  Y

<400> SEQUENCE: 21
gattttgttt gcctgcctcc tgggagcagc ctttgctatg cccgtgagta aaatacccct    60
gcataatatt caatttacaa atggaaataa gaatttgtcc cccagctggg aaactttcca   120
aggtttaaaa cagtttgagc ta                                           142

<210> SEQ ID NO 22
<211> LENGTH: 492
<212> TYPE: DNA
<213> ORGANISM: Canis familiaris  X consensus

<400> SEQUENCE: 22
atggggacct ggattttgtt tgcctgcctc ctgggagcag cctttgctat gcccgtgagt    60
aaaatacccc tgcataatat tcaatttcac aagcttggaa ataaaagtct gccccacagt   120
tggtaaactt tagggtttaa gacagtacaa gatcagatgt cctcaaatgt ctctgtgttt   180
aagaaacact tggaagagct tgttataaaa aaaatatat tcccagatgc ctccacccaa    240
gactgattca gtagagcagg agtgggggga gtgcccagga ctctgcattt taacaagcac   300
ctcaggagat tctgtggaga caattaactt gtaaatatca tcgcccatct ctagatggag   360
gaaactttta gaagggaccc ttgaaaggcc tccagagaaa gtgctcgaac agcttaggca   420 atactacaa aaatgccaat tttctctaaa acccaatttc taacgagtgt ccaactctct    480
tcctgccctc ca                                                      492

<210> SEQ ID NO 23
<211> LENGTH: 680
<212> TYPE: DNA
<213> ORGANISM: Canis familiaris  Y consensus

<400> SEQUENCE: 23
atggggacct ggattttgtt tgcctgcctc ctgggagcag ccttcagtat gcctgtgagt    60
```

```
aaaatttcca atttccaatt tcacaagctt ggaaataaaa atctgcctca gattttatt        120 tagggttaaa tttaagggtt taagacagta caagatctga tgttcacaaa tgtgactgtg        180
tttaagaaac attttaaaa tcttgatcac aagattttaa aacaaaaaca ttctcagttg        240
ccttcaccca tattctgatt cagtatagcc agagtggggg gtgtgctgag aactctgaat        300
tttaacaagc aagaacctca ggaaattctt ggaaacaatt acttataatc actcatctct        360
agatggaaaa tttttggaag ggacctttga aaggcctcca gaaaaagtgc tcaatcagtc        420
tttaagtact acaaaaatgc cagttttctc taaaaccaaa tttctcacaa gtatctaact        480
ctctttctgc tcagaaaacc cccgggctat cattcttcag agtaagattt cagtgttagg        540
aatttccttc ctgaactatt tatttgtcag tcacctgcta agcagatgac ttcctattgg        600
ttgtccagaa tgcatgtggg tatagtttac attcaaatgt accaagggat agggaatgt        660 ggtaactgag agacagacac                                                  680
```

<210> SEQ ID NO 24
<211> LENGTH: 64
<212> TYPE: DNA
<213> ORGANISM: Homo sapiens  X

<400> SEQUENCE: 24

```
atgggacct ggattttatt tgcctgcctc ctgggagcag cttttgccat gcctgtgagt         60
aaaa                                                                    64
```

<210> SEQ ID NO 25
<211> LENGTH: 18
<212> TYPE: PRT
<213> ORGANISM: Homo sapiens  X

<400> SEQUENCE: 25

Met Gly Thr Trp Ile Leu Phe Ala Cys Leu Leu Gly Ala Ala Phe Ala
1               5                   10                  15

Met Pro

<210> SEQ ID NO 26
<211> LENGTH: 64
<212> TYPE: DNA
<213> ORGANISM: Homo sapiens  Y

<400> SEQUENCE: 26

```
atgggacct ggattttgtt tgcctgcctt gtgggagcag cttttgccat gcctgtgagt         60
aaaa                                                                    64
```

<210> SEQ ID NO 27
<211> LENGTH: 18
<212> TYPE: PRT
<213> ORGANISM: Homo sapiens  Y

<400> SEQUENCE: 27

Met Gly Thr Trp Ile Leu Phe Ala Cys Leu Val Gly Ala Ala Phe Ala
1               5                   10                  15

Met Pro

<210> SEQ ID NO 28
<211> LENGTH: 64
<212> TYPE: DNA
<213> ORGANISM: Canis familiaris  X

```
<400> SEQUENCE: 28
atggggacct ggattttgtt tgcctgcctc ctgggagcag cctttgctat gcccgtgagt    60
aaaa                                                                 64

<210> SEQ ID NO 29
<211> LENGTH: 18
<212> TYPE: PRT
<213> ORGANISM: Canis familiaris  X

<400> SEQUENCE: 29

Met Gly Thr Trp Ile Leu Phe Ala Cys Leu Leu Gly Ala Ala Phe Ala
1               5                   10                  15

Met Pro

<210> SEQ ID NO 30
<211> LENGTH: 64
<212> TYPE: DNA
<213> ORGANISM: Canis familiaris  Y

<400> SEQUENCE: 30
atggggacct ggattttgtt tgcctgcctc ctgggagcag ccttcagtat gcctgtgagt    60
aaaa                                                                 64

<210> SEQ ID NO 31
<211> LENGTH: 18
<212> TYPE: PRT
<213> ORGANISM: Canis familiaris  Y

<400> SEQUENCE: 31

Met Gly Thr Trp Ile Leu Phe Ala Cys Leu Leu Gly Ala Ala Phe Ser
1               5                   10                  15

Met Pro

<210> SEQ ID NO 32
<211> LENGTH: 252
<212> TYPE: DNA
<213> ORGANISM: Canis familiaris

<400> SEQUENCE: 32
ccctcacttc tcatacccag actcctcgct gctgctgctg ctgctgcttc ttcttcttct    60
tcttcttctt cttcttcttc ttcttcttct tcttcttctt cttcatatcg aagtatagtt   120
gacatattgt attagattca ggtgtacagc atagtgattc aggtgtacag catagtgatt   180
caacaattaa atgcacttca acattaaaaa atgcctcacc atgttaagtg tagttaccat   240
ctgtcaccat ac                                                       252

<210> SEQ ID NO 33
<211> LENGTH: 234
<212> TYPE: DNA
<213> ORGANISM: Canis familiaris

<400> SEQUENCE: 33
tttgaacgga atatttttaa gtcctgaaga tttgtgaaag tttaacggtt taatgtccaa    60
gtgtgcaaat aaaagtaaaa ttataaagca tgctatcttg tttcccacag catttctaaa   120
ttttatttat ttatttattt atttatttat ttatttattt atttacactt tctaaatttt   180
aatgacaatg ttgtatacag tgaaacctct cattaatttg aaaaacagca aaga          234
```

<210> SEQ ID NO 34
<211> LENGTH: 279
<212> TYPE: DNA
<213> ORGANISM: Canis familiaris

<400> SEQUENCE: 34

```
tacacaggaa tgagaagaat gatatgcctg ctgaaaacct tttcagcact tgaagggatg      60
agcactgggt gttatactat atgttggcaa atcgaacttc aataaaaaaa agaagaaaga     120
aagaagaaag aaggaaagag aaagaaaaag aaagaaagaa agaaagaaag aaagaaagaa     180
agaaagaaag aaagaaagaa agaaaacctt tcaaacttct agtttgacaa tgcaattgtg     240
tattaggaaa gggagttgca atatatagac ctctccaga                            279
```

<210> SEQ ID NO 35
<211> LENGTH: 475
<212> TYPE: DNA
<213> ORGANISM: Canis familiaris
<220> FEATURE:
<221> NAME/KEY: misc_feature
<222> LOCATION: (10)..(10)
<223> OTHER INFORMATION: n is any nucleotide

<400> SEQUENCE: 35

```
ctttcagggn aactcctgcc ctcctgggag tccaaagcct tttcttttac cctgatttgt      60
cctttctcaa atacccagac tctaaagtgg caacattaaa tatgctaact ccatttaaaa     120
gtgccatttg agggcagccc tggtggctca gtggtttagc gctgcctaca gcctagggcg     180
tgatcctgga gacctgggat tgagtccac gtcgggctcc ctgcatggag cctgcttctc      240
cctctgcctg tgtctctgcc tctctctctg tgtctctcat aaataaataa ataaataaat     300
aaataaataa ataaatctta aaaaaaaaat agaagtgcca tttgatgtct tcatctattg     360
atgactcaat caagttttatt atctacttca agttgctcta gctgaaatca agagtcggga    420
cgctcaacca agtgagccct ccaggtaccc cacaaatgtt gatagttcaa acttt         475
```

<210> SEQ ID NO 36
<211> LENGTH: 427
<212> TYPE: DNA
<213> ORGANISM: Canis familiaris

<400> SEQUENCE: 36

```
tttctcctct cttctaagat gatcacttct actctactgg gatctctgaa ggggatccca      60
ataatggcat cctgcttcat gcaggggtgc tgaacaagtt gagagataaa gcaacaggca     120
aatatgaagg taaacatatc gactttatca ctgtgggagg ctaaattgga ggtgtacttt     180
gtctttctcc tttctttctt tctttctttc tttctttctt tctttctttc tttctttctt     240 ttgcttttttg ttagattgtg tttatttatt tgagagaaag agagtggagg gaggggcaga    300
ctgagaggga gaagtagact ccatggtgag caggagcct gatgagacat gaggctccat      360
cccaggaccc tgggaccata acctgagcta ttttctctga acaaaggcac tgctgaggta     420
gttcaag                                                              427
```

<210> SEQ ID NO 37
<211> LENGTH: 454
<212> TYPE: DNA
<213> ORGANISM: Canis familiaris

<400> SEQUENCE: 37

```
tgcagttttt gaagaaactc ctgaaataag ggcagagaca agagaggaag gagaaaggga      60
```

```
ggtgaccctg tgaacgcctg aacttaatcc tggacagaca ccccttccct ggtacttcta      120 ttttccaaa  acgaaagaaa gaaaaaaaa  gaccaaaaaa agaaaaaaag aaagaaaaa       180 gaaagaaaga aagaaagaaa gaaagaaaga agaaagaaa  gaaagaaaga agaaaaaga      240 aagaaagaaa gaaagaaaga aagaaagaaa gaaagaaaga agaaagaaa  gaaagaaaga      300 aagaaaagtg aattagaact catttatctt tgttaacttt cctcattgtt ggataactgt     360
accggtgtta tttaaggaaa tactattgaa gtatgccggg gaacaggacc atgatgtcta     420
ccacttattc tcaagtggtt tggagaaaaa gaat                                  454

<210> SEQ ID NO 38
<211> LENGTH: 394
<212> TYPE: DNA
<213> ORGANISM: Canis familiaris

<400> SEQUENCE: 38
tattaatgat attttagata gtaatttcca gttctgcatt catatcagaa tttaatgttt      60
aaaaactata ctgtataaaa acctgccttt gtaaatgtaa gaaatattg  ggtatatact     120 ttggatgaat ggatggagaa gaaacttatt ttatatgatt ttaaaagtgt aggattatgg     180
gaatatacac atatacactt tgtgtgcatt tcagtgtttt taaaacatta aaatttttct     240
tttttctttt tcttttcttt tctctctctc tttcttctt  tctttctttc tttctttctt     300
tctttctttc tttctttctt tctttctttc tttctttctt tctttctttt gcttgtcttg     360
gatagatact tcaatgaagg tctgcatgct tcta                                 394

<210> SEQ ID NO 39
<211> LENGTH: 344
<212> TYPE: DNA
<213> ORGANISM: Canis familiaris
<220> FEATURE:
<221> NAME/KEY: misc_feature
<222> LOCATION: (176)..(176)
<223> OTHER INFORMATION: n is any nucleotide

<400> SEQUENCE: 39
ttaacattct ctgcctctcc ctttgcccct ctcaccctc  taaaaaaaaa aaagaaaaa       60 agaaagaaag aaagaaagaa agaaagaaag aaagaaagaa agaaagaaag aaagaaagaa     120
actctagaca gaagagatta tccacaaatt gatacaattt gggatataag attggnagaa     180
ggtttcctat aagaacaata ctagaaaata ttaatatatt taaggaattc aaagggaaag     240
tttctaacaa gcaattgaac acaggttatg gtaacacatg ctggtaattt gtaaatttga     300
ttaactggca tgttattagg aatgcttact tgtttggaga ctaa                     344

<210> SEQ ID NO 40
<211> LENGTH: 334
<212> TYPE: DNA
<213> ORGANISM: Canis familiaris
<220> FEATURE:
<221> NAME/KEY: misc_feature
<222> LOCATION: (1)..(334)
<223> OTHER INFORMATION: n is any nucleotide

<400> SEQUENCE: 40
tgaatttcta tatataatag gactncttta aactatggtt ccnagaaaaa tgggaaaatn      60
ctatatatct cattttctag tccccagtct agttcactgc ccgcctgacc aacatccacc     120
agtgatagtg aaaattaaa  gaaaaacctg nncaaataaa taataaata  aataaatgaa     180 tgaatgaaaa aagaaagaa  agaaagaaag aagaaagaa  agaaagaaag aaagaaagaa     240
```

```
agaaagaaag aaagaaagaa agaaaggaaa gagacctgtn ccgaattaaa tcaccagact    300
gggggaggcc tntctgtgat atgaaaataa ctga                                334

<210> SEQ ID NO 41
<211> LENGTH: 206
<212> TYPE: DNA
<213> ORGANISM: Canis familiaris
<220> FEATURE:
<221> NAME/KEY: misc_feature
<222> LOCATION: (194)..(194)
<223> OTHER INFORMATION: n is any nucleotide

<400> SEQUENCE: 41
ctgtgagatc tcctaaatta gaggtctaac cataaaagtt tagtcctcta acaacctaag    60
caaaaataaa taaataaata aataaataaa taaataaata aataaataaa taaataaaaa    120
aaaatttctc tctaggattt tcccctacca gtttgttgtt taattcctgg gagaggagca    180
cattcccgct tagnagcaca ttctag                                         206

<210> SEQ ID NO 42
<211> LENGTH: 460
<212> TYPE: DNA
<213> ORGANISM: Canis familiaris

<400> SEQUENCE: 42
tgctgtatgt gaggctccct ctccctacaa ggctcctctc ctctttccaa gaaatccaaa    60
tactcatcct ctgagaccca gcccaaatgc cccctcctcc agaaagcact cagtgcagga    120
gtcctgcagg cacgcacagg gggaccccaa gcgaacacct tcagacctca ctcatgtatg    180
acgggtatga tgtctttgtg gcagggttat gactgggggg ttaacagagc tcctgtcatg    240
atctcagggt tgtgggattg agccccactc aggctccgtg ctcagcaccg agtctgcttg    300
agattctctc ttcctctccc tctcctcctc ccttgtgttc tctctttctt gaatgaatga    360
atgaaagaaa gaaagaaaga aagaaagaaa gaaagaaaga agaaagaaa gaaaatttat    420 aagggaaaga atttttatat cataggggttc ctagaacagg                         460

<210> SEQ ID NO 43
<211> LENGTH: 335
<212> TYPE: DNA
<213> ORGANISM: Canis familiaris
<220> FEATURE:
<221> NAME/KEY: misc_feature
<222> LOCATION: (327)..(327)
<223> OTHER INFORMATION: n is any nucleotide

<400> SEQUENCE: 43
tgattgttca tgcaaaaagt aattgctcag cgcctgccac atatcaagca tcgctttgag    60
tgcttttgaa agaatatgga caaagtcaat gtcctttgtg agtttgtgat cttatgcaac    120
aaccggttgt gatttctggg ccaaattatc caaaaataaa taaataaata aataaataaa    180
taaataaata aataaataaa agatgtcact aatgacacag aaatggagga taagactttc    240
ctggtctaaa aaaagatca agaacaaacc ataataaatg ccaaatgtgt ctatactgag    300
gtgaagtgta aatgatatg taaccantcg gagca                                335

<210> SEQ ID NO 44
<211> LENGTH: 388
<212> TYPE: DNA
<213> ORGANISM: Canis familiaris
```

```
<400> SEQUENCE: 44
taactctgaa aacaactcaa agactggcag aagagcctct ccacctttga acatagatgg        60
gaaaccacac tgaaaagagt agaaagggct aaattggtat aatcagtggg gcttaactcc       120
aagttcattt gttctttctt tcttcctttc ttttcttct ttctttcttt ctttctttct       180
ttctttcttt ctttctttct ttctttcttt ctctttcttt cttccttcct tcctttattt       240
aaagatttta tttatttatt tatttataca tggaggaaga ggcagaggag agggagaggg       300
ataagcagac tctgtactga atatggagcc agaattgagg gtggatccct aaccctgggg       360
tcagggactg agctatttcc tctcataa                                           388

<210> SEQ ID NO 45
<211> LENGTH: 348
<212> TYPE: DNA
<213> ORGANISM: Canis familiaris
<220> FEATURE:
<221> NAME/KEY: misc_feature
<222> LOCATION: (187)..(345)
<223> OTHER INFORMATION: n is any nucleotide

<400> SEQUENCE: 45
tgctctttgt aaaatgacct gaaagaaagg aaagaaagaa agaagaaaga aagaaagaaa        60
gaaagaaaga aagaaagaaa gaaagaaaga aagaaagaaa ggaaggaagg aaggaaggaa       120
ggaagaaagg aagaaagaaa gaaaggaaga aagaaagagt gtgccaaact gccctgatgt       180
cagtagnatc agtctacatg aagtaatgac ccgaactgaa accctaaacc catatggcta       240
gtagaatatc tgtggttaat aatgtttatg taatccaaat aaagttaatg ggttttagga       300
cgattcccag ggttagttaa ggncaangag aattaatttg ggatntga                    348

<210> SEQ ID NO 46
<211> LENGTH: 497
<212> TYPE: DNA
<213> ORGANISM: Canis familiaris

<400> SEQUENCE: 46
ttaaggcatc tgcaaagcag caagaacaca gccttagttt aatacaataa attatgtttg        60
caatgaggaa cttgccttct gcagaaggct ggaatcctgt ttaataattt gtgtttaaga       120
aggcatcaaa ttagagaatg tattttatta aaacgcacat gaaaatagtc actccaaaaa       180
agattagtgc tgaaggagat atatcaacat tttacttttg ttcccacagc tcaggttgtg       240
atctcagact catgatatca agacccacat caggctcttt gctcagtgct aagtctcttt       300
aagtttctct ttccctctgc tcctccccac gtgcatactc tctctactgt cttgctctct       360
ctcaaataaa taaataaata aataaataaa taaataaata aataaatcta tctttaaaaa       420
agtaaagaaa gtcatacaaa taagcatctg aaaagataca caacatcatg agtcaaaaga       480
atcaatgaca agcecttt                                                      497

<210> SEQ ID NO 47
<211> LENGTH: 251
<212> TYPE: DNA
<213> ORGANISM: Canis familiaris

<400> SEQUENCE: 47
tagtttgtcc tgattatgac ccacacaaaa gcccacgaac tagcatttgg ctaatgtgtc        60
tctcaagccg gttttgtaac aaatctccct ctcctcctct ttttttttat tttttctga        120 tgttatttgt ttttatttat ttatttattt atttattttat ttatttattt atttatttat      180
```

```
ttattttgat attatttgtt aaataaagaa gttaggtcat gtggtctgta gatctcccca    240
ttctggatcc a                                                         251
```

```
<210> SEQ ID NO 48
<211> LENGTH: 350
<212> TYPE: DNA
<213> ORGANISM: Canis familiaris
<220> FEATURE:
<221> NAME/KEY: misc_feature
<222> LOCATION: (1)..(346)
<223> OTHER INFORMATION: n is any nucleotide

<400> SEQUENCE: 48
ntatcatntg gatagagaat ctgagtcagn ggngagatat naaattttc tntgaaaaag     60 tagattagat ctcaggcagt tacaagcagt gattagagtt atcttataca aaaaaaaga    120 aaaaaagaaa gaaagaaaaa gaagaaagaa agaaagaaag aaagaaagaa agaaagaaag   180
aaagaaagaa gaaagataaa atggntttgc caatcagaaa atnttttgct cagcagaana   240
taaagaaaaa gagagtcata gaggnaagca ttgncgaggt gcactgntta gagaatgcct   300
aggncctgag ccacacccta ccaggaccta gangctccac ccnggnaggt              350
```

```
<210> SEQ ID NO 49
<211> LENGTH: 376
<212> TYPE: DNA
<213> ORGANISM: Canis familiaris
<220> FEATURE:
<221> NAME/KEY: misc_feature
<222> LOCATION: (4)..(4)
<223> OTHER INFORMATION: n is any nucleotide

<400> SEQUENCE: 49
tatnccatca gagaagataa agcaattctc aaaaattgga ataattggaa taagaccata    60
aaacaaccca aagacataca aaaaagagaa agaagaaaga aagaaagaaa gaagaagaa   120 agaaagaaag aaagaaagaa agaaagaaag aaagaaagaa gaaagaaaga agagaaaaa   180 gaaaagaaaa aagaaaaaga aaagaaaaa gaaagaaaa agaaaaaaag attcgaggag    240
agattaatga cttagaacac agaaaataga ataaataaat ctggaagctt ctgtttcttt   300
ttacactgtc aggaatatg ccacagacaa ggagagggga agtcaatatt taattccgga   360
atcacaacgt tccccc                                                  376
```

```
<210> SEQ ID NO 50
<211> LENGTH: 299
<212> TYPE: DNA
<213> ORGANISM: Canis familiaris
<220> FEATURE:
<221> NAME/KEY: misc_feature
<222> LOCATION: (101)..(101)
<223> OTHER INFORMATION: n is any nucleotide

<400> SEQUENCE: 50
tcaggtcatg atctcaggtt tgtgagatcg agcccccaatg tcgaattcca tggtgaacgt    60
ggaacctgct taagattctc ttgctctccc tctctcactg ncccaccctg ttcgcatgct   120
ctccctctga agaaagaaa gaagaaaga agaaagaaa gaaagaaaga aagaaagaa     180 gaaagaaaga agaaaaaag agtaagtata gacctagaaa acgagattcc tattccactt   240
tcattatggt atggagaagt tcagtccctt agggtaaag tttgtctttg ggaggctga    299
```

```
<210> SEQ ID NO 51
```

```
<211> LENGTH: 475
<212> TYPE: DNA
<213> ORGANISM: Canis familiaris
<220> FEATURE:
<221> NAME/KEY: misc_feature
<222> LOCATION: (61)..(292)
<223> OTHER INFORMATION: n is any nucleotide

<400> SEQUENCE: 51
tgataaccag ggaggaaatt gaagcaatca tcaaaaactt ccaagacaca aagtccaggg      60
ncagatggct tcccagggga attctatcaa atgtttatag aagaaacaat acctactctc     120 ttatttttt tatattttaa aatattgcaa taaatattac tttgttactg aggtgtcttt     180
ttttattgtt gttgttgttg ttgttgttgt tgttgttgtt gttgtnntga catcgcctcc     240
aaaacgaaga cttcacttgc ttcatcttaa ttctgggttn gtgatatttg gnccccagat     300
taaatttaaa aatgctgaat aaatttctaa atcacagccc ttgaatatga acaatgacac     360
tgtatcaagg gaaggaagga aggaaggaag gaaggaagga aggaaggaag gaaggaagga     420
aggaaggaaa gaaggaaggc agagggaggg agcataggca gttagagagg aagga          475

<210> SEQ ID NO 52
<211> LENGTH: 20
<212> TYPE: DNA
<213> ORGANISM: Artificial sequence
<220> FEATURE:
<223> OTHER INFORMATION: Primer

<400> SEQUENCE: 52
cacttctcat acccagactc                                                  20

<210> SEQ ID NO 53
<211> LENGTH: 20
<212> TYPE: DNA
<213> ORGANISM: Artificial sequence
<220> FEATURE:
<223> OTHER INFORMATION: Primer

<400> SEQUENCE: 53
atgagcactg ggtgttatac                                                  20

<210> SEQ ID NO 54
<211> LENGTH: 20
<212> TYPE: DNA
<213> ORGANISM: Artificial sequence
<220> FEATURE:
<223> OTHER INFORMATION: Primer

<400> SEQUENCE: 54
atcctggaga cctgggattg                                                  20

<210> SEQ ID NO 55
<211> LENGTH: 20
<212> TYPE: DNA
<213> ORGANISM: Artificial sequence
<220> FEATURE:
<223> OTHER INFORMATION: Primer

<400> SEQUENCE: 55
tatcgacttt atcactgtgg                                                  20

<210> SEQ ID NO 56
<211> LENGTH: 20
<212> TYPE: DNA
<213> ORGANISM: Artificial sequence
```

```
<220> FEATURE:
<223> OTHER INFORMATION: Primer

<400> SEQUENCE: 56
acgcctgaac ttaatcctgg                                               20

<210> SEQ ID NO 57
<211> LENGTH: 20
<212> TYPE: DNA
<213> ORGANISM: Artificial sequence
<220> FEATURE:
<223> OTHER INFORMATION: Primer

<400> SEQUENCE: 57
gctatcttgt ttcccacagc                                               20

<210> SEQ ID NO 58
<211> LENGTH: 20
<212> TYPE: DNA
<213> ORGANISM: Artificial sequence
<220> FEATURE:
<223> OTHER INFORMATION: Primer

<400> SEQUENCE: 58
cctgcctttg taaatgtaag                                               20

<210> SEQ ID NO 59
<211> LENGTH: 20
<212> TYPE: DNA
<213> ORGANISM: Artificial sequence
<220> FEATURE:
<223> OTHER INFORMATION: Primer

<400> SEQUENCE: 59
attctctgcc tctcccttttg                                              20

<210> SEQ ID NO 60
<211> LENGTH: 27
<212> TYPE: DNA
<213> ORGANISM: Artificial sequence
<220> FEATURE:
<223> OTHER INFORMATION: Primer

<400> SEQUENCE: 60
tctagtcccc agtctagttc actgccc                                       27

<210> SEQ ID NO 61
<211> LENGTH: 20
<212> TYPE: DNA
<213> ORGANISM: Artificial sequence
<220> FEATURE:
<223> OTHER INFORMATION: Primer

<400> SEQUENCE: 61
cctaaattag aggtctaacc                                               20

<210> SEQ ID NO 62
<211> LENGTH: 20
<212> TYPE: DNA
<213> ORGANISM: Artificial sequence
<220> FEATURE:
<223> OTHER INFORMATION: Primer

<400> SEQUENCE: 62
ctcagcaccg agtctgcttg                                               20
```

<210> SEQ ID NO 63
<211> LENGTH: 20
<212> TYPE: DNA
<213> ORGANISM: Artificial sequence
<220> FEATURE:
<223> OTHER INFORMATION: Primer

<400> SEQUENCE: 63
aaccggttgt gatttctggg                                         20

<210> SEQ ID NO 64
<211> LENGTH: 20
<212> TYPE: DNA
<213> ORGANISM: Artificial sequence
<220> FEATURE:
<223> OTHER INFORMATION: Primer

<400> SEQUENCE: 64
tggggcttaa ctccaagttc                                         20

<210> SEQ ID NO 65
<211> LENGTH: 20
<212> TYPE: DNA
<213> ORGANISM: Artificial sequence
<220> FEATURE:
<223> OTHER INFORMATION: Primer

<400> SEQUENCE: 65
gctctttgta aaatgacctg                                         20

<210> SEQ ID NO 66
<211> LENGTH: 20
<212> TYPE: DNA
<213> ORGANISM: Artificial sequence
<220> FEATURE:
<223> OTHER INFORMATION: Primer

<400> SEQUENCE: 66
tttgctcagt gctaagtctc                                         20

<210> SEQ ID NO 67
<211> LENGTH: 20
<212> TYPE: DNA
<213> ORGANISM: Artificial sequence
<220> FEATURE:
<223> OTHER INFORMATION: Primer

<400> SEQUENCE: 67
ctaatgtgtc tctcaagccg                                         20

<210> SEQ ID NO 68
<211> LENGTH: 20
<212> TYPE: DNA
<213> ORGANISM: Artificial sequence
<220> FEATURE:
<223> OTHER INFORMATION: Primer

<400> SEQUENCE: 68
gtagattaga tctcaggcag                                         20

<210> SEQ ID NO 69
<211> LENGTH: 20
<212> TYPE: DNA
<213> ORGANISM: Artificial sequence
<220> FEATURE:
<223> OTHER INFORMATION: Primer

```
<400> SEQUENCE: 69
gagaagataa agcaattctc                                              20

<210> SEQ ID NO 70
<211> LENGTH: 20
<212> TYPE: DNA
<213> ORGANISM: Artificial sequence
<220> FEATURE:
<223> OTHER INFORMATION: Primer

<400> SEQUENCE: 70
gtggaacctg cttaagattc                                              20

<210> SEQ ID NO 71
<211> LENGTH: 20
<212> TYPE: DNA
<213> ORGANISM: Artificial sequence
<220> FEATURE:
<223> OTHER INFORMATION: Primer

<400> SEQUENCE: 71
gcccttgaat atgaacaatg                                              20

<210> SEQ ID NO 72
<211> LENGTH: 20
<212> TYPE: DNA
<213> ORGANISM: Artificial sequence
<220> FEATURE:
<223> OTHER INFORMATION: Primer

<400> SEQUENCE: 72
caatatgtca actatacttc                                              20

<210> SEQ ID NO 73
<211> LENGTH: 20
<212> TYPE: DNA
<213> ORGANISM: Artificial sequence
<220> FEATURE:
<223> OTHER INFORMATION: Primer

<400> SEQUENCE: 73
caatatgtca actatacttc                                              20

<210> SEQ ID NO 74
<211> LENGTH: 20
<212> TYPE: DNA
<213> ORGANISM: Artificial sequence
<220> FEATURE:
<223> OTHER INFORMATION: Primer

<400> SEQUENCE: 74
gattgagtca tcaatagatg                                              20

<210> SEQ ID NO 75
<211> LENGTH: 20
<212> TYPE: DNA
<213> ORGANISM: Artificial sequence
<220> FEATURE:
<223> OTHER INFORMATION: Primer

<400> SEQUENCE: 75
atggagcctc atgtctcatc                                              20

<210> SEQ ID NO 76
```

-continued

```
<211> LENGTH: 20
<212> TYPE: DNA
<213> ORGANISM: Artificial sequence
<220> FEATURE:
<223> OTHER INFORMATION: Primer

<400> SEQUENCE: 76
acagttatcc aacaatgagg                                          20

<210> SEQ ID NO 77
<211> LENGTH: 20
<212> TYPE: DNA
<213> ORGANISM: Artificial sequence
<220> FEATURE:
<223> OTHER INFORMATION: Primer

<400> SEQUENCE: 77
tcactgtata caacattgtc                                          20

<210> SEQ ID NO 78
<211> LENGTH: 20
<212> TYPE: DNA
<213> ORGANISM: Artificial sequence
<220> FEATURE:
<223> OTHER INFORMATION: Primer

<400> SEQUENCE: 78
cttcattgaa gtatctatcc                                          20

<210> SEQ ID NO 79
<211> LENGTH: 20
<212> TYPE: DNA
<213> ORGANISM: Artificial sequence
<220> FEATURE:
<223> OTHER INFORMATION: Primer

<400> SEQUENCE: 79
tgtggataat ctcttctgtc                                          20

<210> SEQ ID NO 80
<211> LENGTH: 20
<212> TYPE: DNA
<213> ORGANISM: Artificial sequence
<220> FEATURE:
<223> OTHER INFORMATION: Primer

<400> SEQUENCE: 80
agtctggtga tttaattcgg                                          20

<210> SEQ ID NO 81
<211> LENGTH: 20
<212> TYPE: DNA
<213> ORGANISM: Artificial sequence
<220> FEATURE:
<223> OTHER INFORMATION: Primer

<400> SEQUENCE: 81
taagcgggaa tgtgctcctc                                          20

<210> SEQ ID NO 82
<211> LENGTH: 20
<212> TYPE: DNA
<213> ORGANISM: Artificial sequence
<220> FEATURE:
<223> OTHER INFORMATION: Primer

<400> SEQUENCE: 82
```
cctgttctag gaaccctatg　　　　　　　　　　　　　　　　　　　　　　　　20

<210> SEQ ID NO 83
<211> LENGTH: 20
<212> TYPE: DNA
<213> ORGANISM: Artificial sequence
<220> FEATURE:
<223> OTHER INFORMATION: Primer

<400> SEQUENCE: 83
tctgtgtcat tagtgacatc　　　　　　　　　　　　　　　　　　　　　　　　20

<210> SEQ ID NO 84
<211> LENGTH: 20
<212> TYPE: DNA
<213> ORGANISM: Artificial sequence
<220> FEATURE:
<223> OTHER INFORMATION: Primer

<400> SEQUENCE: 84
cagtacagag tctgcttatc　　　　　　　　　　　　　　　　　　　　　　　　20

<210> SEQ ID NO 85
<211> LENGTH: 20
<212> TYPE: DNA
<213> ORGANISM: Artificial sequence
<220> FEATURE:
<223> OTHER INFORMATION: Primer

<400> SEQUENCE: 85
tgggaatcgt cctaaaaccc　　　　　　　　　　　　　　　　　　　　　　　　20

<210> SEQ ID NO 86
<211> LENGTH: 20
<212> TYPE: DNA
<213> ORGANISM: Artificial sequence
<220> FEATURE:
<223> OTHER INFORMATION: Primer

<400> SEQUENCE: 86
gactcatgat gttgtgtatc　　　　　　　　　　　　　　　　　　　　　　　　20

<210> SEQ ID NO 87
<211> LENGTH: 20
<212> TYPE: DNA
<213> ORGANISM: Artificial sequence
<220> FEATURE:
<223> OTHER INFORMATION: Primer

<400> SEQUENCE: 87
tggggagatc tacagaccac　　　　　　　　　　　　　　　　　　　　　　　　20

<210> SEQ ID NO 88
<211> LENGTH: 20
<212> TYPE: DNA
<213> ORGANISM: Artificial sequence
<220> FEATURE:
<223> OTHER INFORMATION: Primer

<400> SEQUENCE: 88
taggtcctgg tagggtgtgg　　　　　　　　　　　　　　　　　　　　　　　　20

<210> SEQ ID NO 89
<211> LENGTH: 20
<212> TYPE: DNA

```
<213> ORGANISM: Artificial sequence
<220> FEATURE:
<223> OTHER INFORMATION: Primer

<400> SEQUENCE: 89
aagtcattaa tctctcctcg                                                    20

<210> SEQ ID NO 90
<211> LENGTH: 20
<212> TYPE: DNA
<213> ORGANISM: Artificial sequence
<220> FEATURE:
<223> OTHER INFORMATION: Primer

<400> SEQUENCE: 90
ctaagggact gaacttctcc                                                    20

<210> SEQ ID NO 91
<211> LENGTH: 20
<212> TYPE: DNA
<213> ORGANISM: Artificial sequence
<220> FEATURE:
<223> OTHER INFORMATION: Primer

<400> SEQUENCE: 91
tcctctctaa ctgcctatgc                                                    20

<210> SEQ ID NO 92
<211> LENGTH: 22
<212> TYPE: DNA
<213> ORGANISM: Artificial sequence
<220> FEATURE:
<223> OTHER INFORMATION: Primer

<400> SEQUENCE: 92
gccttattca ttgcagttag gg                                                 22

<210> SEQ ID NO 93
<211> LENGTH: 18
<212> TYPE: DNA
<213> ORGANISM: Artificial sequence
<220> FEATURE:
<223> OTHER INFORMATION: Primer

<400> SEQUENCE: 93
cagccgagca catggttt                                                      18

<210> SEQ ID NO 94
<211> LENGTH: 21
<212> TYPE: DNA
<213> ORGANISM: Artificial sequence
<220> FEATURE:
<223> OTHER INFORMATION: Primer

<400> SEQUENCE: 94
aaatggaaca gttgagcatg c                                                  21

<210> SEQ ID NO 95
<211> LENGTH: 22
<212> TYPE: DNA
<213> ORGANISM: Artificial sequence
<220> FEATURE:
<223> OTHER INFORMATION: Primer

<400> SEQUENCE: 95
atgctgagtt ttgaactttc cc                                                 22
```

-continued

```
<210> SEQ ID NO 96
<211> LENGTH: 21
<212> TYPE: DNA
<213> ORGANISM: Artificial sequence
<220> FEATURE:
<223> OTHER INFORMATION: Primer

<400> SEQUENCE: 96
attgattctg atatgcccag c                                              21

<210> SEQ ID NO 97
<211> LENGTH: 21
<212> TYPE: DNA
<213> ORGANISM: Artificial sequence
<220> FEATURE:
<223> OTHER INFORMATION: Primer

<400> SEQUENCE: 97
ccccttacag cttcattttc c                                              21

<210> SEQ ID NO 98
<211> LENGTH: 20
<212> TYPE: DNA
<213> ORGANISM: Artificial sequence
<220> FEATURE:
<223> OTHER INFORMATION: Primer

<400> SEQUENCE: 98
ggctgtcact tttccctttc                                                20

<210> SEQ ID NO 99
<211> LENGTH: 24
<212> TYPE: DNA
<213> ORGANISM: Artificial sequence
<220> FEATURE:
<223> OTHER INFORMATION: Primer

<400> SEQUENCE: 99
caccacaatc tctctcataa atac                                           24
```